US010001468B2

(12) United States Patent
Kamp et al.

(10) Patent No.: US 10,001,468 B2
(45) Date of Patent: Jun. 19, 2018

(54) BIOMARKERS FOR DIFFERENTIATING BETWEEN NON-ALCOHOLIC STEATOHEPATITIS (NASH) AND NON-ALCOHOLIC FATTY LIVER DISEASE (NAFLD)

(71) Applicants: METANOMICS HEALTH GMBH, Berlin (DE); UNIVERSITÄTSKLINIKUM SCHLESWIG-HOLSTEIN, Kiel (DE)

(72) Inventors: Hennicke Kamp, Bischheim (DE); Ulrike Rennefahrt, Berlin (DE); Jens Fuhrmann, Berlin (DE); Dietrich Rein, Berlin (DE); Jochen Hampe, Kiel (DE); Clemens Schafmayer, Kiel (DE)

(73) Assignees: METANOMICS HEALTH GMBH, Berlin (DE); UNIVERSITATSKLINIKUM SCHLESWIG-HOLSTEIN, Kiel (DE)

( * ) Notice: Subject to any disclaimer, the term of this patent is extended or adjusted under 35 U.S.C. 154(b) by 0 days. days.

(21) Appl. No.: 14/828,925

(22) Filed: Aug. 18, 2015

(65) Prior Publication Data
US 2015/0355197 A1 Dec. 10, 2015

Related U.S. Application Data

(62) Division of application No. 13/703,203, filed as application No. PCT/EP2011/059650 on Jun. 10, 2011, now Pat. No. 9,140,686.

(60) Provisional application No. 61/353,249, filed on Jun. 10, 2010.

(30) Foreign Application Priority Data

Jun. 10, 2010 (EP) .................................... 10165554

(51) Int. Cl.
G01N 33/68 (2006.01)
G01N 33/50 (2006.01)
G01N 33/92 (2006.01)

(52) U.S. Cl.
CPC ......... *G01N 33/50* (2013.01); *G01N 33/6812* (2013.01); *G01N 33/6893* (2013.01); *G01N 33/92* (2013.01); *G01N 2800/085* (2013.01)

(58) Field of Classification Search
None
See application file for complete search history.

(56) References Cited

U.S. PATENT DOCUMENTS

| 4,540,884 | A | 9/1985 | Stafford et al. |
| 5,397,894 | A | 3/1995 | Wells et al. |
| 8,808,979 | B2* | 8/2014 | van Ravenzwaay .. G01N 33/66 425/25 |
| 9,140,686 | B2* | 9/2015 | Kamp ................ G01N 33/6812 |
| 9,186,343 | B2* | 11/2015 | Barker .................... A61K 31/20 |
| 2005/0103991 | A1 | 5/2005 | Walk et al. |
| 2007/0178442 | A1 | 8/2007 | Wienhues-Thelen et al. |
| 2010/0197028 | A1 | 8/2010 | Watkins et al. |
| 2010/0233724 | A1* | 9/2010 | Watkins ................. G01N 33/92 435/7.1 |
| 2010/0279956 | A1* | 11/2010 | McCreedy, Jr. ... G01N 33/6893 514/23 |
| 2011/0009279 | A1* | 1/2011 | Younossi ........... G01N 33/6893 506/7 |
| 2011/0092592 | A1* | 4/2011 | Yano .................... A61K 31/202 514/549 |
| 2011/0113863 | A1 | 5/2011 | Fuhrmann et al. |
| 2011/0166162 | A1 | 7/2011 | von Deyn et al. |
| 2011/0313276 | A1* | 12/2011 | Cales ................. G01N 33/6893 600/410 |
| 2012/0132797 | A1 | 5/2012 | Strauss et al. |
| 2012/0157397 | A1* | 6/2012 | Hazen ................... C12Q 1/025 514/39 |
| 2012/0209535 | A1 | 8/2012 | Prokoudine et al. |
| 2012/0238028 | A1 | 9/2012 | Reszka et al. |
| 2012/0286157 | A1 | 11/2012 | Fuhrmann et al. |
| 2014/0005500 | A1 | 1/2014 | Cales et al. |
| 2015/0377910 | A1* | 12/2015 | McCreedy ......... G01N 33/6893 506/9 |

FOREIGN PATENT DOCUMENTS

| EP | 1582873 A1 | 10/2005 |
| EP | 2157431 A1 | 2/2010 |
| WO | WO-03/073464 A1 | 9/2003 |
| WO | WO-2008/021192 A2 | 2/2008 |
| WO | WO-2009/059150 A2 | 5/2009 |
| WO | WO-2010/018165 A1 | 2/2010 |
| WO | WO-2012/085890 A1 | 6/2012 |
| WO | WO-2012/164026 A1 | 12/2012 |

OTHER PUBLICATIONS

Loomba R. et al. Polyunsaturated Fatty Acid Metabolites as Novel Lipidomic Biomarkers for Noninvasive Diagnosis of NASH. J of Lipid Research 56(1)185-192, 2015.*
Bell L. et al. Serum Proteomics and Biomarker Discovery Across the Spectrum of NAFLD. Hepatology 51(1)111-120, Jan. 2010.
Brunt, E. M., "Pathology of Nonalcoholic Fatty Liver Disease", Nature Reviews, 2010, vol. 7, pp. 195-203.
Brunt, E. M., et al., "Nonalcoholic Steatohepatitis: A Proposal for Grading and Staging the Histological Lesions", The American Journal of Gastroenterology, 1999, vol. 94, No. 9, pp. 2467-2474.
Carulli, L., et al., "Genetic Polymorphisms in Non-Alcoholic Fatty Liver Disease: Interleukin-6-174G/C Polymorphism is Associated with Non-Alcoholic Steatohepatitis", Digestive and Liver Disease, 2009, vol. 41, pp. 823-828.
International Preliminary Report on Patentability for PCT/EP2011/059650 dated Dec. 10, 2012.

(Continued)

Primary Examiner — Ralph J Gitomer
(74) Attorney, Agent, or Firm — Marshall, Gerstein & Borun LLP

(57) ABSTRACT

The present invention provides biomarkers and a method for differentiating between NASH and NAFLD in a subject.

1 Claim, No Drawings

(56) References Cited

OTHER PUBLICATIONS

International Search Report for PCT/EP2011/059650 dated Oct. 21, 2011.
Karbownik, M., et al., "Indole-3-Propionic Acid, a Melatonin-Related Molecule, Protects Hepatic Microsomal Membranes from Iron-Induced Oxidative Damage: Relevance to Cancer Reduction", Journal of Cellular Biochemistry, 2001, vol. 81, pp. 507-513.
Kashi, M. R., et al., "Current and Emerging Therapies in Nonalcoholic Fatty Liver Disease", Seminars in Liver Disease, 2008, vol. 28, No. 4, pp. 396-406.
Lee J. et al. Serum Uric Acid as a Predictor for the Devleopment of NAFLD in Apparently Healthy Subjects. Gut and Liver 4(3)378-383, Sep. 2010.
Niessen, W. M. A., et al., "Liquid Chromatography-Mass Spectrometry General Principles and Instrumentation", Journal of Chromatography A, 1995, vol. 703, pp. 37-57.
Poynard T. et al. The Diagnostic Value of Biomarkers (SteatoTest) for the Prediction of Liver Steatosis. Comparative Hepatology 4(10)1-14, Dec. 23, 2005.
Provost J. et al. Plasma Triglycerides: An Overlooked Biomarker of Hepatotoxicity in the Rat. Comparative Clinical Pathology 12(2)95-101, Sep. 2003.
Puri, P., et al., "A Lipidomic Analysis of Nonalcoholic Fatty Liver Disease", Hepatology, 2007, vol. 46, pp. 1081-1090.
Raghavendran H. et al. Effect of Sargassum polycystum (Phaeophyceae) Sulphated Polysaccharide Extract . . . Molecular and Cellular Biochemistry 276(1-2)89-96, Aug. 2005.
Sanyal, A. J., "AGA Technical Review on Nonalcoholic Fatty Liver Disease", Gastroenterology, 2002, vol. 123, pp. 1705-1725.
Vuppalanchi, R., et al., "Nonalcoholic Fatty Liver Disease and Nonalcoholic Steatohepatitis: Selected Practical Issues in their Evaluation and Management", Hepatology, 2008, vol. 49, pp. 306-317.
Wieckowska A. et al. Diagnosis of Nonalcoholic Fatty Liver Disease: Invasive vs. Noninvasive. Seminars in Liver Disease 28(4)386-395, 2008.
Yamada, H., et al., "Dansyl Chloride Derivatization of Methamphetamine: A Method with Advantages for Screening and Analysis of Methamphetamine in Urine", Journal of Analytical Toxicology, 2002, vol. 26, No. 1, pp. 17-22.
Yoneda, M., et al., "Association Between Angiotensin II Type 1 Receptor Polymorphisms and the Occurrence of Nonalcoholic Fatty Liver Disease", Liver International, 2009, vol. 29, No. 7, pp. 1078-7085.
Kalhan et al., Plasma Metabolomic Profile in Non-Alcoholic Fatty Liver Disease, 60(3):Supplemental Table (2011).
European Search Report in EP 17 186 813.6 dated Oct. 13, 2017.
Kalhan, S., et al., "Plasma Metabolomic Profile in Nonalcoholic Fatty Liver Disease", Metabolism Clinical and Experimental, 2011, vol. 60, pp. 404-13.
Makowski, L., et al., "Metabolic profiling of $PPAR^{\alpha/-}$ Mice Reveals Defects in Carnitine and Amino Acid Homeostasis That Are Partially Reversed by Oral Carnitine Supplementation", The FASEB Journal, 2017, vol. 23, No. 2, pp. 586-604.
Mukherjee, S., et al., "Role of Plasma Amino Acids and GABA in Alcoholic and Non-Alcoholic Fatty Liver Disease—A Pilot Study", Indian Journal of Clinical Biochemistry, 2010, vol. 25 No. 1, pp. 37-42.
Roberts, E., "Pediatric Nonalcoholic Fatty Liver Disease (NAFLD): A 'Growing' Problem?", Journal of Hepatology, 2007, vol. 46, pp. 1133-1142.
Yoneda, M., et al., "Life Style-Related Diseases of the Digestive System: Gene Expression in Nonalcoholic Steatohepatitis Patients and Treatment Strategies", J Pharm Sci, 2007, vol. 105, pp. 151-156.

\* cited by examiner

BIOMARKERS FOR DIFFERENTIATING BETWEEN NON-ALCOHOLIC STEATOHEPATITIS (NASH) AND NON-ALCOHOLIC FATTY LIVER DISEASE (NAFLD)

RELATED APPLICATIONS

This application is a divisional application of U.S. application Ser. No. 13/703,203, filed Dec. 10, 2012, now U.S. Pat. No. 9,140,686, which is a national stage application (under 35 U.S.C. §371) of PCT/EP2011/059650, filed Jun. 10, 2011, which claims benefit of U.S. Provisional Application No. 61/353,249, filed Jun. 10, 2010, and European application 10165554.6, filed Jun. 10, 2010.

BACKGROUND OF THE INVENTION

The present invention relates to the field of diagnostic methods. Specifically, the present invention contemplates a method for diagnosing a liver disease in a subject and a method of differentiating between NASH and NAFLD. The invention also relates to tools for carrying out the aforementioned methods, such as diagnostic devices.

Fatty liver disease that develops in the absence of alcohol abuse is recognized increasingly as a major health burden, in particular if an inflammatory component is involved such as in non-alcoholic steatohepatitis (NASH). Estimates based on imaging and biopsy studies suggest that about 20% to 30% of adults in the United States and other Western countries have excess fat accumulation in the liver. About 10% of these individuals, or fully 2% to 3% of adults, are estimated to meet current diagnostic criteria for NASH. Sustained liver injury leads to progressive fibrosis and cirrhosis in about 30% of NASH patients. The diagnostic criteria for NASH continue to evolve and rely on the histologic findings of steatosis, hepatocellular injury (ballooning, Mallory bodies), and the pattern of fibrosis.

Liver biopsy has remained the criterion standard or "gold standard" in the evaluation of the etiology and extent of disease of the liver such as non-alcoholic fatty liver disease (NAFLD) and NASH. Percutaneous liver biopsy is the preferred method to determine NAFLD and to differentiate NASH from NAFLD. Other biopsy methods are typically even more invasive and include transvenous and laparoscopic liver biopsy. The American Gastroenterological Association has published detailed recommendations on how to grade NAFLD comprising NASH into macrovesicular steatosis grades, necroinflammatory activity grades and fibrosis stages (American Gastroenterological Association 2002, Gastroenterology 123: 1705-25; Brunt 1999, Am J Gastroenterol. 94: 2467-74, Brunt 2010, Nat Rev Gastroenterol Hepatol. 7:195-203).

Although liver biopsies are generally regarded as safe, they bare risks that are potentially lethal. Almost two thirds of complications of liver biopsy occur within two hours. Approximately 2% of patients undergoing liver biopsy require hospitalization for the management of an adverse event. Significant bleeding after a liver biopsy occurs in approximately 1% of patients who are biopsied. If bleeding persists, a blood transfusion may be needed. Surgery or angiography, where the bleeding site is identified and treated, may be required if the bleeding is severe or does not stop on its own. Intraperitoneal hemorrhage is the most serious consequence of bleeding. Fatal complications have been reported in up to 0.04% of biopsied patients.

An additional challenge for the liver biopsy is the cost associated with the diagnosis. The costs for liver biopsy and histological assessment were estimated to be above USD 1000 for needle biopsies without complications and above USD 2700 with complications. Moreover, biopsy assessment of the type and severity of hepatic steatosis is associated with a significant time investment for the practitioner and the patient for examination and post-biopsy care.

Metabolite biomarker based methods which either analyze blood or tissue samples have been recently reported for diagnosing fatty liver diseases; see WO 2009/059150 and WO 2010/018165. Other biomarkers, such as lipids, noninvasive imaging or scoring systems are also known and are described, e.g., in Vuppalanchi 2009, Hepatology, 49:306-317; Pun 2007, Hepatology 46:1081-1090.

Thus, a robust minimal invasive test to reliably and efficiently diagnose NASH and differentiate the inflammatory indication NASH from the less harmful NAFLD without inflammatory component is needed.

SUMMARY OF THE INVENTION

Accordingly, the technical problem underlying the present invention could be seen as the provision of means and methods for diagnosing a fatty liver disease, or predisposition therefor which avoids the aforementioned drawbacks of invasive technologies. The technical problem is solved by the embodiments characterized in the claims and herein below.

Therefore, the present invention relates to a method for diagnosing a liver disease, or a predisposition therefor in a subject comprising the steps of:
(a) determining in a sample of a subject suspected to suffer from a liver disease the amount of at least one biomarker from Tables 1A, 1a, 1B, 1b, 2A, 2a, 2b, 3A, 3a, 3B, 3b, 4A, 4a, 4B or 4b and
(b) comparing the said amount of the at least one biomarker with a reference, whereby a liver disease or a predisposition is to be diagnosed.

DETAILED DESCRIPTION OF THE INVENTION

The method as referred to in accordance with the present invention includes a method which essentially consists of the aforementioned steps or a method which includes further steps. However, it is to be understood that the method, in a preferred embodiment, is a method carried out ex vivo, i.e. not practised on the human or animal body. The method, preferably, can be assisted by automation.

The term "diagnosing" as used herein refers to assessing whether a subject suffers from the liver disease, or not. As will be understood by those skilled in the art, such an assessment, although preferred to be, may usually not be correct for 100% of the investigated subjects. The term, however, requires that a statistically significant portion of subjects can be correctly assessed and, thus, diagnosed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% or at least 95%. The p-values are, preferably, 0.2, 0.1, or 0.05.

The term includes individual diagnosis of liver disease, or its symptoms as well as continuous monitoring of a patient. Monitoring, i.e. diagnosing the presence or absence of liver disease or the symptoms accompanying it at various time points, includes monitoring of subjects known to suffer from liver disease as well as monitoring of subjects known to be at risk of developing liver disease. Furthermore, monitoring can also be used to determine whether a subject is treated successfully or whether at least symptoms of liver disease can be ameliorated over time by a certain therapy. The term, furthermore, includes the diagnosis of a particular type of liver disease, preferably, inflammatory liver disease or, more preferably, fatty liver disease. Preferably said fatty liver disease is steatosis, non-alcoholic steatohepatitis (NASH) or non-alcoholic fatty liver disease (NAFDL). The differential diagnosis of steatosis, inflammatory liver disease, NASH and NAFDL, and, particularly, of steatosis, NASH and NAFDL can be achieved as described elsewhere herein.

Diagnosing as used herein also refers to diagnosing a predisposition of a liver disease and, thus, predicting whether a subject is at increased risk of developing a liver disease within a predictive window starting from the time when the sample to be analyzed has been taken. Preferably, the predictive window is at least three months, six months, one year, two years, five years, ten years or up to the entire life span of the subject. A subject is at increased risk if the probability by which it will develop the disease is statistically significantly increased with respect to the average or mean probability, i.e. the prevalence for the disease in the respective population from which analyzed subject originates. Again, it is to be understood that such a diagnosis of a predisposition although preferred may not be correct in each case. However, it is envisaged that a statistically significant portion of subjects of a cohort can be correctly diagnosed for having the predisposition.

The term "liver disease" as used herein, preferably, relates to a disease that affects liver function. More preferably, the term relates to inflammatory liver disease. Most preferably, the term relates to fatty liver disease.

The "inflammatory liver disease", preferably, refers to a liver disease which involves the activation and recruitment of inflammatory cells to the liver. The inflammatory liver disease may be accompanied by steatosis (such as NASH, see elsewhere herein) or, more preferably, not be accompanied by steatosis. Inflammatory liver disease is, preferably, caused by viral infection, bacterial load, drugs, chemical intoxication and environmental contamination.

Viral infections that cause inflammatory liver disease are, preferably, infection with HAV (hepatitis A virus), HBV (hepatitis B virus), HCV (hepatitis C virus), HDV (hepatitis D virus), HEV (hepatitis E virus), CMV (cytomegalovirus), EBV (Epstein-Barr virus). Accordingly, the method of the present invention, preferably, allows for a diagnosis of inflammatory liver disease in a subject suffering from hepatitis A, B, C, D or E, from Epstein-Barr virus infection, or from cytomegalovirus infection. More preferably, the subject suffers from hepatitis C. Moreover, also envisaged is the diagnosis of hepatitis A, B, C, D or E, from Epstein-Barr virus infection, or from cytomegalovirus infection.

Drugs or chemicals that cause inflammatory liver disease are well known in the art. Preferred drugs and/or chemicals are carbon-tetrachloride, amethopterin, tetracycline, acetaminophen, fenoprofen, cyclopeptides, monomethylhydrazine, sulphamethizole, urolucosil, sulphacetamide amd silver sulphadiazine. Accordingly, the method of the present invention allows for diagnosing inflammatory liver disease in subjects after contact with said drugs or chemicals (e.g. by direct intake or by skin contact).

The term "fatty liver disease" is well known in the art. Preferably, the term refers to an impairment of the liver. Preferably, said impairment is the result of a surplus of triacylglyceride that accumulate in the liver and form large vacuoles. The symptoms accompanying fatty liver disease are well known from standard text books of medicine such as Stedman's or Pschyrembel. Fatty liver disease may result from alcohol abuse, diabetes mellitus, nutritional defects and wrong diets, toxicity of drugs or genetic predisposition (see Carulli et al. 2009, Dig Liver Dis. 41(11):823-8. Epub 2009 Apr. 28 "Genetic polymorphisms in non-alcoholic fatty liver disease: interleukin-6-174G/C polymorphism is associated with non-alcoholic steatohepatitis"; or Yoneda et al. 2009, Liver Int. 29(7):1078-85. Epub 2009 Mar. 3 "Association between angiotensin II type 1 receptor polymorphisms and the occurrence of nonalcoholic fatty liver disease"). Fatty liver disease as used in accordance with the present invention also include the more severe forms thereof and, in particular, steatosis, NASH or NAFDL. Symptoms accompanying these diseases are also well known to the physicians and are described in detail in standard text books of medicine.

In accordance with the present invention, specific biomarkers for individual subtypes of liver disease are provided as well so that the method of the present invention does not only allow for diagnosing liver disease but also a particular subtype of liver disease, e.g. fatty liver disease or inflammatory liver disease. For diagnosing fatty liver disease the at least one biomarker, preferably, is from Tables 1A, 1a, 1B, 1b, 3A, 3a, 3B, 3b, 4A, 4a, 4B or 4b.

Preferably, the method of the present invention allows for diagnosing an inflammatory liver disease. Thus, preferably, the at least one biomarker is from table 2A, 2a, or 2b.

Preferably, the method of the present invention allows for diagnosing a particular subtype of fatty liver disease. Thus, preferably, the at least one biomarker is
(i) from Table 1A, 1a 1B, or 1b, wherein the fatty liver disease is steatosis,
(ii) from Table 3A, 3a, 3B or 3b, wherein the fatty liver disease is NASH or
(iii) from Table 4A, 4a, 4B or 4b, wherein the fatty liver disease is NAFLD.

Thus the method of the present invention allows for diagnosing the following subtypes of liver disease: steatosis, inflammatory liver disease, NASH or NAFLD. Thus, preferably, the at least one biomarker is
(i) from Table 1A, 1a 1B, or 1b, wherein the liver disease is steatosis,
(ii) from table 2A, 2a, or 2b, wherein the liver disease is inflammatory liver disease,
(iii) from Table 3A, 3a, 3B or 3b, wherein the liver disease is NASH or
(iv) from Table 4A, 4a, 4B or 4b, wherein the liver disease is NAFLD.

The term "biomarker" as used herein refers to a molecular species which serves as an indicator for a disease or effect as referred to in this specification. Said molecular species can be a metabolite itself which is found in a sample of a subject. Moreover, the biomarker may also be a molecular species which is derived from said metabolite. In such a case, the actual metabolite will be chemically modified in the sample or during the determination process and, as a result of said modification, a chemically different molecular species, i.e. the analyte, will be the determined molecular species. It is to be understood that in such a case, the analyte represents the actual metabolite and has the same potential as an indicator for the respective medical condition as the original metabolite would have.

Moreover, a biomarker according to the present invention is not necessarily corresponding to one molecular species. Rather, the biomarker may comprise stereoisomers or enantiomeres of a compound. Further, a biomarker can also represent the sum of isomers of a biological class of isomeric molecules. Said isomers shall exhibit identical analytical characteristics in some cases and are, therefore, not distinguishable by various analytical methods including those applied in the accompanying Examples described below. However, the isomers will share at least identical sum formula parameters and, thus, in the case of, e.g., lipids an identical chain length and identical numbers of double bonds in the fatty acid and/or sphingo-base moieties.

In the method according to the present invention, at least one biomarker of the biomarkers shown in Tables 1A, 1a, 1B, 1b, 2A, 2a, 2b, 3A, 3a, 3B, 3b, 4A, 4a, 4B or 4b is to be determined. However, more preferably, a group of biomarkers will be determined in order to strengthen specificity and/or sensitivity of the assessment. Such a group, preferably, comprises at least 2, at least 3, at least 4, at least 5, at least 10 or up to all of the said biomarkers shown in the Tables 1A, 1a, 1B, 1b, 2A, 2a, 2b, 3A, 3a, 3B, 3b, 4A, 4a, 4B or 4b.

A metabolite as used herein refers to at least one molecule of a specific metabolite up to a plurality of molecules of the said specific metabolite. It is to be understood further that a group of metabolites means a plurality of chemically different molecules wherein for each metabolite at least one molecule up to a plurality of molecules may be present. A metabolite in accordance with the present invention encompasses all classes of organic or inorganic chemical compounds including those being comprised by biological material such as organisms. Preferably, the metabolite in accordance with the present invention is a small molecule compound. More preferably, in case a plurality of metabolites is envisaged, said plurality of metabolites representing a metabolome, i.e. the collection of metabolites being comprised by an organism, an organ, a tissue, a body fluid or a cell at a specific time and under specific conditions.

In addition to the specific biomarkers recited in the specification, other biomarkers may be, preferably, determined as well in the methods of the present invention. Such biomarkers may include metabolite biomarkers, peptide or polypeptide biomarkers or scoring system based biomarkers and, in particular, those disclosed in any one of WO 2009/059150, WO 2010/018165, US2010279956, US2010197028, or Vuppalanchi 2009, Hepatology, 49:306-317; Puri 2007, Hepatology 46:1081-1090, the disclosure content of which is, in this respect, herewith incorporated by reference.

The term "sample" as used herein refers to samples from body fluids, preferably, blood, plasma, serum, saliva or urine, or samples derived, e.g., by biopsy, from cells, tissues or organs, in particular from the liver. More preferably, the sample is a blood, plasma or serum sample, most preferably, a plasma sample. Biological samples can be derived from a subject as specified elsewhere herein. Techniques for obtaining the aforementioned different types of biological samples are well known in the art. For example, blood samples may be obtained by blood taking while tissue or organ samples are to be obtained, e.g., by biopsy as described elsewhere herein. In a preferred embodiment of the method of the present invention, the sample is a blood, serum or plasma sample and the at least one metabolite is from Tables 1A, 1B, 2A, 3A, 3B, 4A, or 4B. In another preferred embodiment of the method of the present invention, the sample is a liver tissue sample and the at least one biomarker is from Tables 1a, 1b, 2a, 2b, 3a, 3b, 4a, or 4b.

The aforementioned samples are, preferably, pre-treated before they are used for the method of the present invention. As described in more detail below, said pre-treatment may include treatments required to release or separate the compounds or to remove excessive material or waste. Suitable techniques comprise centrifugation, extraction, fractioning, ultrafiltration, protein precipitation followed by filtration and purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pre-treatments depend on the means used for carrying out the method of the invention and are well known to the person skilled in the art. Pre-treated samples as described before are also comprised by the term "sample" as used in accordance with the present invention.

The term "subject" as used herein relates to animals and, preferably, to mammals. More preferably, the subject is a primate and, most preferably, a human. The subject, preferably, is suspected to suffer from a liver disease, i.e. it may already show some or all of the symptoms associated with the disease. Preferably, the subject, however, is besides the aforementioned diseases and disorders apparently healthy. The subject may also suffer from a viral infection or may be suspected to suffer from a viral infection as referred to herein.

The said subject, preferably, may also be at increased risk of developing liver disease, i.e. having a predisposition for liver disease. Such a subject may be also apparently healthy with respect to liver disease. A subject being at increased risk may be a subject suffering from diabetes mellitus or an alcohol addict. Moreover, a subject being at increased risk and, thus, having a predisposition for liver disease, may be a subject which is exposed to toxic substances or harmful drugs or which is affected by a wrong nutritional diet or which has a genetic predisposition.

The term "determining the amount" as used herein refers to determining at least one characteristic feature of a biomarker to be determined by the method of the present invention in the sample. Characteristic features in accordance with the present invention are features which characterize the physical and/or chemical properties including biochemical properties of a biomarker. Such properties include, e.g., molecular weight, viscosity, density, electrical charge, spin, optical activity, colour, fluorescence, chemoluminescence, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a biomarker by standard operations, e.g., mathematical calculations such as multiplication, division or logarithmic calculus. Most preferably, the at least one characteristic feature allows the determination and/or chemical identification of the said at least one biomarker and its amount. Accordingly, the characteristic value, preferably, also comprises information relating to the abundance of the biomarker from which the characteristic value is derived. For example, a characteristic value of a biomarker may be a peak in a mass spectrum. Such a peak contains characteristic information of the biomarker, i.e. the m/z information, as well as an intensity value being related to the abundance of the said biomarker (i.e. its amount) in the sample.

As discussed before, each biomarker comprised by a sample may be, preferably, determined in accordance with the present invention quantitatively or semi-quantitatively. For quantitative determination, either the absolute or precise amount of the biomarker will be determined or the relative amount of the biomarker will be determined based on the value determined for the characteristic feature(s) referred to herein above. The relative amount may be determined in a case were the precise amount of a biomarker can or shall not be determined. In said case, it can be determined whether the amount in which the biomarker is present is enlarged or diminished with respect to a second sample comprising said biomarker in a second amount. In a preferred embodiment said second sample comprising said biomarker shall be a calculated reference as specified elsewhere herein. Quantitatively analysing a biomarker, thus, also includes what is sometimes referred to as semi-quantitative analysis of a biomarker.

Moreover, determining as used in the method of the present invention, preferably, includes using a compound separation step prior to the analysis step referred to before. Preferably, said compound separation step yields a time resolved separation of the metabolites comprised by the sample. Suitable techniques for separation to be used preferably in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. Most preferably, LC and/or GC are chromatographic techniques to be envisaged by the method of the present invention. Suitable devices for such determination of biomarkers are well known in the art. Preferably, mass spectrometry is used in particular gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). Most preferably, LC-MS and/or GC-MS are used as described in detail below. Said techniques are disclosed in, e.g., Nissen 1995, Journal of Chromatography A, 703: 37-57, U.S. Pat. No. 4,540,884 or U.S. Pat. No. 5,397,894, the disclosure content of which is hereby incorporated by reference. As an alternative or in addition to mass spectrometry techniques, the following techniques may be used for compound determination: nuclear magnetic resonance (NMR), magnetic resonance imaging (MRI), Fourier transform infrared analysis (FT-IR), ultraviolet (UV) spectroscopy, refraction index (RI), fluorescent detection, radiochemical detection, electrochemical detection, light scattering (LS), dispersive Raman spectroscopy or flame ionisation detection (FID). These techniques are well known to the person skilled in the art and can be applied without further ado. The method of the present invention shall be, preferably, assisted by automation. For example, sample processing or pre-treatment can be automated by robotics. Data processing and comparison is, preferably, assisted by suitable computer programs and databases. Automation as described herein before allows using the method of the present invention in high-throughput approaches.

Moreover, the at least one biomarker can also be determined by a specific chemical or biological assay. Said assay shall comprise means which allow to specifically detect the at least one biomarker in the sample. Preferably, said means are capable of specifically recognizing the chemical structure of the biomarker or are capable of specifically identifying the biomarker based on its capability to react with other compounds or its capability to elicit a response in a biological read out system (e.g., induction of a reporter gene). Means which are capable of specifically recognizing the chemical structure of a biomarker are, preferably, antibodies or other proteins which specifically interact with chemical structures, such as receptors or enzymes. Specific antibodies, for instance, may be obtained using the biomarker as antigen by methods well known in the art. Antibodies as referred to herein include both polyclonal and monoclonal antibodies, as well as fragments thereof, such as Fv, Fab and F(ab)$_2$ fragments that are capable of binding the antigen or hapten. The present invention also includes humanized hybrid antibodies wherein amino acid sequences of a non-human donor antibody exhibiting a desired antigen-specificity are combined with sequences of a human acceptor antibody. Moreover, encompassed are single chain antibodies. The donor sequences will usually include at least the antigen-binding amino acid residues of the donor but may comprise other structurally and/or functionally relevant amino acid residues of the donor antibody as well. Such hybrids can be prepared by several methods well known in the art. Suitable proteins which are capable of specifically recognizing the biomarker are, preferably, enzymes which are involved in the metabolic conversion of the said biomarker. Said enzymes may either use the biomarker as a substrate or may convert a substrate into the biomarker. Moreover, said antibodies may be used as a basis to generate oligopeptides which specifically recognize the biomarker. These oligopeptides shall, for example, comprise the enzyme's binding domains or pockets for the said biomarker. Suitable antibody and/or enzyme based assays may be RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA) or solid phase immune tests. Moreover, the biomarker may also be determined based on its capability to react with other compounds, i.e. by a specific chemical reaction. Further, the biomarker may be determined in a sample due to its capability to elicit a response in a biological read out system. The biological response shall be detected as read out indicating the presence and/or the amount of the biomarker comprised by the sample. The biological response may be, e.g., the induction of gene expression or a phenotypic response of a cell or an organism. In a preferred embodiment the determination of the least one biomarker is a quantitative process, e.g., allowing also the determination of the amount of the at least one biomarker in the sample As described above, said determining of the at least one biomarker can, preferably, comprise mass spectrometry (MS). Mass spectrometry as used herein encompasses all techniques which allow for the determination of the molecular weight (i.e. the mass) or a mass variable corresponding to a compound, i.e. a biomarker, to be determined in accordance with the present invention. Preferably, mass spectrometry as used herein relates to GC-MS, LC-MS, direct infusion mass spectrometry, FT-ICR-MS, CE-MS, HPLC-MS, quadrupole mass spectrometry, any sequentially coupled mass spectrometry such as MS-MS or MS-MS-MS, ICP-MS, Py-MS, TOF or any combined approaches using the aforementioned techniques. How to apply these techniques is well known to the person skilled in the art. Moreover, suitable devices are commercially available. More preferably, mass spectrometry as used herein relates to LC-MS and/or GC-MS, i.e. to mass spectrometry being operatively linked to a prior chromatographic separation step. More preferably, mass spectrometry as used herein encompasses quadrupole MS. Most preferably, said quadrupole MS is carried out as follows: a) selection of a mass/charge quotient (m/z) of an ion created by ionisation in a first analytical quadrupole of the mass spectrometer, b) fragmentation of the ion selected in step a) by applying an acceleration voltage in an additional subsequent quadrupole which is filled with a collision gas and acts as a collision chamber, c) selection of a mass/charge quotient of an ion created by the fragmentation process in step b) in an additional subsequent quadrupole, whereby steps a) to c) of the method are carried out at least once and analysis of the mass/charge quotient of all the ions present in the mixture of substances as a result of the ionisation process, whereby the quadrupole is filled with collision gas but no acceleration voltage is applied during the analysis. Details on said most preferred mass spectrometry to be used in accordance with the present invention can be found in WO 2003/073464.

More preferably, said mass spectrometry is liquid chromatography (LC) MS and/or gas chromatography (GC) MS. Liquid chromatography as used herein refers to all techniques which allow for separation of compounds (i.e. metabolites) in liquid or supercritical phase. Liquid chromatography is characterized in that compounds in a mobile phase are passed through the stationary phase. When compounds pass through the stationary phase at different rates they become separated in time since each individual compound has its specific retention time (i.e. the time which is required by the compound to pass through the system). Liquid chromatography as used herein also includes HPLC. Devices for liquid chromatography are commercially available, e.g. from Agilent Technologies, USA. Gas chromatography as applied in accordance with the present invention, in principle, operates comparable to liquid chromatography. However, rather than having the compounds (i.e. metabolites) in a liquid mobile phase which is passed through the stationary phase, the compounds will be present in a gaseous volume. The compounds pass the column which may contain solid support materials as stationary phase or the walls of which may serve as or are coated with the stationary phase. Again, each compound has a specific time which is required for passing through the column. Moreover, in the case of gas chromatography it is preferably envisaged that the compounds are derivatised prior to gas chromatography. Suitable techniques for derivatisation are well known in the art. Preferably, derivatisation in accordance with the present invention relates to methoxymation and trimethylsilylation of, preferably, polar compounds and transmethylation, methoxymation and trimethylsilylation of, preferably, non-polar (i.e. lipophilic) compounds.

The term "reference" refers to values of characteristic features of each of the biomarker which can be correlated to a medical condition, i.e. the presence or absence of the disease, diseases status or an effect referred to herein. Preferably, a reference is a threshold value (e.g., an amount or ratio of amounts) for a biomarker whereby values found in a sample to be investigated which are higher than or essentially identical to the threshold are indicative for the presence of a medical condition while those being lower are indicative for the absence of the medical condition. It will be understood that also preferably, a reference may be a threshold value for a biomarker whereby values found in a sample to be investigated which are lower or identical than the threshold are indicative for the presence of a medical condition while those being higher are indicative for the absence of the medical condition.

In accordance with the aforementioned method of the present invention, a reference is, preferably, a reference obtained from a sample from a subject or group of subjects known to suffer from a disease or condition to be diagnosed in accordance with the present invention. In such a case, a value for the at least one biomarker found in the test sample being essentially identical is indicative for the presence of the disease. Moreover, the reference, also preferably, could be from a subject or group of subjects known not to suffer from the said disease or condition, preferably, an apparently healthy subject. In such a case, a value for the at least one biomarker found in the test sample being altered with respect to the reference is indicative for the presence of the disease. The same applies mutatis mutandis for a calculated reference being, most preferably, the average or median for the relative or absolute value of the at least one biomarker in a population of individuals from which the subject to be investigated originates. The absolute or relative values of the at least one biomarker of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 or 10,000 subjects. It is to be understood that the subject to be diagnosed by the method of the present invention and the subjects of the said plurality of subjects are of the same species.

In a preferred embodiment of the method of the present invention, said reference is derived from a sample of a subject or group of subjects known not to suffer from the liver disease or the predisposition therefor or is a calculated reference. Preferably, said calculated reference is calculated from such a group of subjects. Preferably, the at least one biomarker is from Tables 1A, 1a, 2A, 2a, 3A, 3a, 4A, or 4a and wherein an increase with respect to the reference is indicative for the liver disease or the predisposition therefor or the at least one biomarker is from Tables 1B, 1b, 2b, 3B, 3b, 4B, or 4b and wherein a decrease with respect to the reference is indicative for the liver disease or the predisposition therefor. More preferably, the at least one biomarker is from Tables 1A, 1a, 3A, 3a, 4A, or 4a and wherein an increase with respect to the reference is indicative for the fatty liver disease or the predisposition therefor or the at least one biomarker is from Tables 1B, 1b, 3B, 3b, 4B, or 4b and wherein a decrease with respect to the reference is indicative for the fatty liver disease or the predisposition therefor. Preferably, the at least one biomarker is from Tables 2A or 2a, and wherein an increase with respect to the reference is indicative for the inflammatory liver disease or the predisposition therefor or the at least one biomarker is from Table 2b and wherein a decrease with respect to the reference is indicative for the inflammatory liver disease or the predisposition therefor.

In another preferred embodiment of the method of the present invention, said reference is derived from a sample of a subject or group of subjects known to suffer from the liver disease or the predisposition therefor. Preferably, the at least one biomarker is from Tables 1A, 1a, 2A, 2a, 3A, 3a, 4A, or 4a and wherein a decrease with respect to the reference is indicative for the liver disease or the predisposition therefor or the at least one biomarker is from Tables 1B, 1b, 2b, 3B, 3b, 4B, or 4b and wherein an increase with respect to the reference is indicative for the liver disease or the predisposition therefor.

The value for the at least one biomarker of the test sample and the reference values are essentially identical, if the values for the characteristic features and, in the case of quantitative determination, the intensity values are essentially identical. Essentially identical means that the difference between two values is, preferably, not significant and shall be characterized in that the values for the intensity are within at least the interval between $1^{st}$ and $99^{th}$ percentile, $5^{th}$ and $95^{th}$ percentile, $10^{th}$ and $90^{th}$ percentile, $20^{th}$ and $80^{th}$ percentile, $30^{th}$ and $70^{th}$ percentile, $40^{th}$ and $60^{th}$ percentile of the reference value, preferably, the $50^{th}$, $60^{th}$, $70^{th}$, $80^{th}$, $90^{th}$ or $95^{th}$ percentile of the reference value. Statistical test for determining whether two amounts are essentially identical are well known in the art and are also described elsewhere herein.

An observed difference for two values, on the other hand, shall be statistically significant. A difference in the relative or absolute value is, preferably, significant outside of the interval between $45^{th}$ and $55^{th}$ percentile, $40^{th}$ and $60^{th}$ percentile, $30^{th}$ and $70^{th}$ percentile, $20^{th}$ and $80^{th}$ percentile, $10^{th}$ and $90^{th}$ percentile, $5^{th}$ and $95^{th}$ percentile, $1^{st}$ and $99^{th}$ percentile of the reference value. Preferred changes and ratios of the medians are described in the accompanying Tables as well as in the Examples.

Preferably, the reference, i.e. values for at least one characteristic feature of the at least one biomarker or ratios thereof, will be stored in a suitable data storage medium such as a database and are, thus, also available for future assessments.

The term "comparing" refers to determining whether the determined value of a biomarker is essentially identical to a reference or differs therefrom. Preferably, a value for a biomarker is deemed to differ from a reference if the observed difference is statistically significant which can be determined by statistical techniques referred to elsewhere in this description. If the difference is not statistically significant, the biomarker value and the reference are essentially identical. Based on the comparison referred to above, a subject can be assessed to suffer from the disease, or not.

For the specific biomarkers referred to in this specification, preferred values for the changes in the relative amounts or ratios (i.e. the estimated changes expressed as the ratios of the medians) are found in the Tables, below. The ratios of medians for the biomarkers shown in any one of Tables 1A, 1a, 1B, 1b, 2A, 2a, 2b, 3A, 3a, 3B, 3b, 4A, 4a, 4b or 4B, below, are, preferably, at least the quantitative changes expressed as ratio of medians which are preferably indicative for the liver disease.

The comparison is, preferably, assisted by automation. For example, a suitable computer program comprising algorithms for the comparison of two different data sets (e.g., data sets comprising the values of the characteristic feature(s)) may be used. Such computer programs and algorithms are well known in the art. Notwithstanding the above, a comparison can also be carried out manually.

Advantageously, it has been found in the study underlying the present invention that the amounts of the specific biomarkers referred to above are indicators for liver disease or a predisposition therefor, particularly for fatty liver disease, or a predisposition therefor, or for inflammatory liver disease. Moreover, there are biomarkers provided which allow for identification of subtypes of fatty liver disease such as steatosis, NASH or NAFDL, and, in particular, for the differentiation of the life threatening NASH from the less severe NAFLD. Specifically, in accordance with the present invention, the problem of diagnosing NASH and differentiating NASH from NAFLD and from associated liver diseases was solved by the identification of panels of appropriate metabolite (up to 1500 Dalton) biomarkers that can indicate the type of liver disease and the grade of fat infiltration when measured quantitative in blood plasma. Liver biopsies are generally regarded as safe. However, they bare risks that are potentially lethal. Fatal complications have been reported in up to 0.04% of biopsied patients. Thanks to the present invention, NASH and the inflammatory indication NASH can be efficiently and reliably diagnosed and differentiated from the less harmful NAFLD without inflammatory component, e.g., by diagnosis based on body fluids such as plasma samples. In addition to these health-related advantages, an analysis via a body fluid metabolite profile might be significantly less cost intensive than the gold standard liver biopsy with subsequent histopathology. This is particularly helpful for an efficient diagnosis of the disease as well as for improving of the preclinical and clinical management of liver disease, particularly of fatty liver disease and/or of inflammatory liver disease as well as an efficient monitoring of patients. Moreover, based on the methods according to the present invention, the development of therapeutic measures including drugs can be facilitated and guided. Further, therapies or life style recommendations which are applied can be easily monitored for success without taking a serious risk of adverse side effects caused by the monitoring method.

The definitions and explanations of the terms made above apply mutatis mutandis for the following embodiments of the present invention except specified otherwise herein below.

In light of the foregoing, the method of the present invention can be used for i) monitoring a subject suffering from liver disease, i.e. disease progression or amelioration can be determined, ii) identifying a subject in need of a therapy of liver disease, iii) identifying whether a therapy against liver disease is successful in a subject.

The present invention, therefore, also relates to a method for identifying whether a subject is in need for a therapy of liver disease comprising the steps of the methods of the present invention and the further step of identifying a subject in need if the liver disease is diagnosed.

The phrase "in need for a therapy of liver disease" as used herein means that the disease in the subject is in a status where therapeutic intervention is necessary or beneficial in order to ameliorate or treat the liver disease or the symptoms associated therewith. Accordingly, the findings of the studies underlying the present invention do not only allow diagnosing liver disease or a predisposition therefor in a subject but also allow for identifying subjects which should be treated by a therapy. Once the subject has been identified, the method may further include a step of making recommendations for a therapy of liver disease. Moreover, by analyzing the biomarkers which were found to be specific for inflammatory liver disease, or for a subtype of fatty liver disease, i.e., steatosis, NASH or NAFLD, a more specific therapy can be selected by the aforementioned method. Thus, the method, preferably includes the step of making recommendations for a therapy of steatosis, inflammatory liver disease, NASH or NAFLD wherein the at least one biomarker is (i) from Table 1A, 1a 1B, or 1b and wherein the recommended therapy of (fatty) liver disease is a therapy for treating steatosis, (ii) from table 2A, 2a, or 2b, and wherein the recommended therapy of liver disease is a therapy for treating inflammatory liver disease, (iii) from Table 3A, 3a, 3B or 3b, and wherein the recommended therapy of (fatty) liver disease is a therapy for treating NASH or (iv) from Table 4A, 4a, 4B or 4b, and wherein the recommended therapy of (fatty) liver disease is a therapy for treating NAFLD.

The aforementioned method can be applied mutatis mutandis for recommending a change in a therapy for liver disease.

A therapy of fatty liver disease as used in accordance with the present invention, preferably, comprises surgery, drug treatment or life style recommendations. Drug-based therapies, preferably, include the administration of one or more drugs selected from Statins, Incretin analogues, Metformin, Rimonabant, Thiazolidinediones, Orlistat (see Maryam R. Kashi, Dawn M. Torres, and Stephen A. Harrison: Current and Emerging Therapies in Nonalcoholic Fatty Liver Disease: Therapeutic Modalities; Semin Liver Dis. 2008; 28 (4): 396-406).

The present invention further relates to a method for determining whether a therapy against liver disease is successful in a subject comprising the steps of the methods of the present invention and the further step of determining whether a therapy is successful if no liver disease is diagnosed.

It is to be understood that a liver disease therapy will be successful if liver disease or at least some symptoms thereof are treated or ameliorated compared to an untreated subject with the same kind of liver disease. Moreover, a therapy is also successful as meant herein if the disease progression can be prevented or at least slowed down compared to an untreated subject with the same kind of liver disease.

The definitions given herein above, apply mutatis mutandis to the following (except stated otherwise.

Further, the present invention pertains to a method for differentiating between NASH and NAFLD in a subject comprising:

(a) determining in a sample of a subject suspected to suffer from either NASH or NAFLD the amount of at least one biomarker from Tables 5A or 5B; and (b) comparing the said amount of the at least one biomarker with a reference, whereby it is differentiated whether the subject suffers from NASH or NAFLD.

The term "sample" has been defined herein above. In a preferred embodiment of the aforementioned method of the present invention, the sample is a blood, serum or plasma sample and the at least one metabolite is from Tables 5A or 5B.

The term "differentiating" as used herein refers to determining whether the subject to be analysed suffers from either NAFLD or NASH. The said subject is, preferably, known to suffer from a fatty liver disease.

In a preferred method of the present invention referred to before, said reference is derived from a subject or a group of subjects known to suffer from NAFLD.

Preferably, the at least one biomarker is from Table 5A and wherein an increased amount with respect to the reference is indicative for NASH or the at least one biomarker is from Table 5B and wherein a decreased amount with respect to the reference is indicative for NASH.

In another preferred method of the present invention mentioned before, said reference is derived from a subject or a group of subjects known to suffer from NASH.

Preferably, the at least one biomarker is from Table 5A and wherein a decreased amount with respect to the reference is indicative for NAFLD or the at least one biomarker is from Table 5B and wherein an increased amount with respect to the reference is indicative for NAFLD.

The aforementioned differential diagnosis allows for a more efficient treatment, in particular, of the life threatening condition NASH. Whether a subject suffers at all from a fatty liver disease, or not, can be diagnosed with the method of the present invention pertaining to diagnosing a fatty liver disease in a subject described elsewhere herein. In a particular preferred embodiment of the methods of the present invention, both methods are combined, i.e. it will be diagnosed first whether the subject suffers from a fatty liver disease and subsequently, in particular if NASH or NAFLD has been diagnosed, it is differentiated whether the condition which has been diagnosed is NASH or NAFLD as a confirmation of the primary diagnosis.

The present invention also encompasses a device for diagnosing liver disease or the predisposition therefor in a sample of a subject comprising:

a) an analyzing unit for the said sample of the subject comprising a detector for at least one biomarker from Tables 1A, 1a, 1B, 1b, 2A, 2a, 2b, 3A, 3a, 3B, 3b, 4A, 4a, 4B or 4b, said detector allowing for the determination of the amount of the said at least one biomarker in the sample; and operatively linked thereto, (b) an evaluation unit comprising a data processing unit and a data base, said data base comprising a stored reference for the at least one biomarker and said data processing unit being capable of (i) carrying out a comparison of the amount of the at least one biomarker determined by the analyzing unit and the stored reference and (ii) generating an output information based on which the diagnosis can be established.

Preferred references for the at least one biomarker are described elsewhere herein.

Preferably, said evaluation unit of the aforementioned device comprises a further database allocating (i) the at least one biomarker from Table 1A, 1a 1B, or 1b to the fatty liver disease steatosis, (ii) the at least one biomarker from table 2A, 2a, or 2b to the inflammatory liver disease, (iii) the at least one biomarker from Table 3A, 3a, 3B or 3b to the fatty liver disease NASH and/or (iv) the at least one biomarker from Table 4A, 4a, 4B or 4b to the fatty liver disease NAFLD wherein the data processing unit is capable using this allocation for the generation of the output information based on which a diagnosis can be established that includes the identification of the liver disease as steatosis, inflammatory liver disease, NASH, or NAFLD.

In a preferred embodiment of the device of the present invention, said device is for diagnosing fatty liver disease or the predisposition therefor in a sample of a subject, and comprises:

a) an analyzing unit for the said sample of the subject comprising a detector for at least one biomarker from Tables 1A, 1a, 1B, 1b, 3A, 3a, 3B, 3b, 4A, 4a, 4B or 4b, said detector allowing for the determination of the amount of the said at least one biomarker in the sample; and operatively linked thereto, (b) an evaluation unit comprising a data processing unit and a data base, said data base comprising a stored reference for the at least one biomarker and said data processing unit being capable of (i) carrying out a comparison of the amount of the at least one biomarker determined by the analyzing unit and the stored reference and (ii) generating an output information based on which the diagnosis can be established.

Preferably, said evaluation unit of said device for diagnosing fatty liver disease or the predisposition therefor comprises a further database allocating (i) the at least one biomarker from Table 1A, 1a 1B, or 1b to the fatty liver disease steatosis, (ii) the at least one biomarker from Table 3A, 3a, 3B or 3b to the fatty liver disease NASH and/or (iii) the at least biomarker from Table 4A, 4a, 4B or 4b to the fatty liver disease NAFLD wherein the data processing unit is capable using this allocation for the generation of the output information based on which a diagnosis can be established that includes the identification of the fatty liver disease as steatosis, NASH, or NAFLD.

In another preferred embodiment of said device, said device is for diagnosing inflammatory liver disease or the predisposition therefor in a sample of a subject comprising:
a) an analyzing unit for the said sample of the subject comprising a detector for at least one biomarker from Tables 2A, 2a, or 2b, said detector allowing for the determination of the amount of the said at least one biomarker in the sample; and operatively linked thereto,
(b) an evaluation unit comprising a data processing unit and a data base, said data base comprising a stored reference for the at least one biomarker and said data processing unit being capable of (i) carrying out a comparison of the amount of the at least one biomarker determined by the analyzing unit and the stored reference and (ii) generating an output information based on which the diagnosis can be established.

Preferably, said evaluation unit of said device for diagnosing inflammatory liver disease or the predisposition therefor, preferably, further comprises a database for allocating the at least one biomarker from table 2A, 2a, or 2b to the inflammatory liver disease, wherein the data processing unit is capable using this allocation for the generation of the output information based on which a diagnosis can be established.

The present invention also encompasses a device for determining in a sample of a subject whether the subject to be analysed suffers from either NAFLD or NASH comprising:
b) an analyzing unit for the said sample of the subject comprising a detector for at least one biomarker from Tables 5A or 5B said detector allowing for the determination of the amount of the said at least one biomarker in the sample; and operatively linked thereto,
(b) an evaluation unit comprising a data processing unit and a data base, said data base comprising a stored reference for the at least one biomarker and said data processing unit being capable of (i) carrying out a comparison of the amount of the at least one biomarker determined by the analyzing unit and the stored reference and (ii) generating an output information based on which the determination can be established.

Preferably, the evaluation unit of said device comprises a further database allocating (i) the at least one biomarker from Table 5A or 5B to NASH, and (ii) the at least one biomarker from Table 5A or 5B to NAFLD wherein the data processing unit is capable using this allocation for the generation of the output information based on which a determination can be established that includes whether the subject to be analysed suffers from either NAFLD or NASH.

A device as used herein shall comprise at least the aforementioned units. The units of the device are operatively linked to each other. How to link the means in an operating manner will depend on the type of units included into the device. For example, where the detector allows for automatic qualitative or quantitative determination of the biomarker, the data obtained by said automatically operating analyzing unit can be processed by, e.g., a computer program in order to facilitate the assessment in the evaluation unit. Preferably, the units are comprised by a single device in such a case. Said device may accordingly include an analyzing unit for the biomarker and a computer or data processing device as evaluation unit for processing the resulting data for the assessment and for stabling the output information. Preferred devices are those which can be applied without the particular knowledge of a specialized clinician, e.g., electronic devices which merely require loading with a sample. The output information of the device, preferably, is a numerical value which allows drawing conclusions on the presence or absence of liver disease and, thus, is an aid for diagnosis. More preferably, the output information is a preliminary diagnosis based on the aforementioned numerical value, i.e. a classifier which indicates whether the subject suffers from a liver disease or not. Such a preliminary diagnosis may need the evaluation of further information which can be provided in the device of the invention by including an expert knowledge database system.

Alternatively, the units can be implemented into a system comprising several devices which are operatively linked to each other. Depending on the units to be used for the system of the present invention, said means may be functionally linked by connecting each mean with the other by means which allow data transport in between said means, e.g., glass fiber cables, and other cables for high throughput data transport. Nevertheless, wireless data transfer between the means is also envisaged by the present invention, e.g., via LAN (Wireless LAN, W-LAN). A preferred system comprises means for determining biomarkers. Means for determining biomarkers as used herein encompass means for separating biomarkers, such as chromatographic devices, and means for metabolite determination, such as mass spectrometry devices. Suitable devices have been described in detail above. Preferred means for compound separation to be used in the system of the present invention include chromatographic devices, more preferably devices for liquid chromatography, HPLC, and/or gas chromatography. Preferred devices for compound determination comprise mass spectrometry devices, more preferably, GC-MS, LC-MS, direct infusion mass spectrometry, FT-ICR-MS, CE-MS, HPLC-MS, quadrupole mass spectrometry, sequentially coupled mass spectrometry (including MS-MS or MS-MS-MS), ICP-MS, Py-MS or TOF. The separation and determination means are, preferably, coupled to each other. Most preferably, LC-MS and/or GC-MS are used in the system of the present invention as described in detail elsewhere in the specification. Further comprised shall be means for comparing and/or analyzing the results obtained from the means for determination of biomarkers. The means for comparing and/or analyzing the results may comprise at least one database and an implemented computer program for comparison of the results. Preferred embodiments of the aforementioned systems and devices are also described in detail below.

Furthermore, the present invention relates to a data collection comprising characteristic values of at least one biomarker and the information that the biomarker is indicative for a medical condition or effect as set forth above (i.e. diagnosing liver disease or a predisposition therefor in a subject, or differentiating between NASH and NAFLD).

The term "data collection" refers to a collection of data which may be physically and/or logically grouped together. Accordingly, the data collection may be implemented in a single data storage medium or in physically separated data storage media being operatively linked to each other. Preferably, the data collection is implemented by means of a database. Thus, a database as used herein comprises the data collection on a suitable storage medium. Moreover, the database, preferably, further comprises a database management system. The database management system is, preferably, a network-based, hierarchical or object-oriented database management system. Furthermore, the database may be a federal or integrated database. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative for a medical condition or effect as set forth above (e.g. a query search). Thus, if an identical or similar data set can be identified in the data collection, the test data set will be associated with the said medical condition or effect. Consequently, the information obtained from the data collection can be used, e.g., as a reference for the methods of the present invention described above. More preferably, the data collection comprises characteristic values of all biomarkers comprised by any one of the groups recited above.

In light of the foregoing, the present invention encompasses a data storage medium comprising the aforementioned data collection.

The term "data storage medium" as used herein encompasses data storage media which are based on single physical entities such as a CD, a CD-ROM, a hard disk, optical storage media, or a diskette. Moreover, the term further includes data storage media consisting of physically separated entities which are operatively linked to each other in a manner as to provide the aforementioned data collection, preferably, in a suitable way for a query search.

The present invention also relates to a system comprising:
(a) means for comparing characteristic values of the at least one biomarker of a sample operatively linked to
(b) a data storage medium as described above.

The term "system" as used herein relates to different means which are operatively linked to each other. Said means may be implemented in a single device or may be physically separated devices which are operatively linked to each other. The means for comparing characteristic values of biomarkers, preferably, based on an algorithm for comparison as mentioned before. The data storage medium, preferably, comprises the aforementioned data collection or database, wherein each of the stored data sets being indicative for a medical condition or effect referred to above. Thus, the system of the present invention allows identifying whether a test data set is comprised by the data collection stored in the data storage medium. Consequently, the methods of the present invention can be implemented by the system of the present invention.

In a preferred embodiment of the system, means for determining characteristic values of biomarkers of a sample are comprised. The term "means for determining characteristic values of biomarkers" preferably relates to the aforementioned devices for the determination of metabolites such as mass spectrometry devices, NMR devices or devices for carrying out chemical or biological assays for the biomarkers.

Moreover, the present invention relates to a diagnostic means comprising means for the determination of at least one biomarker selected from any one of the groups referred to above.

The term "diagnostic means", preferably, relates to a diagnostic device, system or biological or chemical assay as specified elsewhere in the description in detail.

The expression "means for the determination of at least one biomarker" refers to devices or agents which are capable of specifically recognizing the biomarker. Suitable devices may be spectrometric devices such as mass spectrometry, NMR devices or devices for carrying out chemical or biological assays for the biomarkers. Suitable agents may be compounds which specifically detect the biomarkers. Detection as used herein may be a two-step process, i.e. the compound may first bind specifically to the biomarker to be detected and subsequently generate a detectable signal, e.g., fluorescent signals, chemiluminescent signals, radioactive signals and the like. For the generation of the detectable signal further compounds may be required which are all comprised by the term "means for determination of the at least one biomarker". Compounds which specifically bind to the biomarker are described elsewhere in the specification in detail and include, preferably, enzymes, antibodies, ligands, receptors or other biological molecules or chemicals which specifically bind to the biomarkers.

Further, the present invention relates to a diagnostic composition comprising at least one biomarker selected from any one of the groups referred to above.

The at least one biomarker selected from any of the aforementioned groups will serve as a biomarker, i.e. an indicator molecule for a medical condition or effect in the subject as set for the elsewhere herein. Thus, the biomarker molecules itself may serve as diagnostic compositions, preferably, upon visualization or detection by the means referred to in herein. Thus, a diagnostic composition which indicates the presence of a biomarker according to the present invention may also comprise the said biomarker physically, e.g., a complex of an antibody and the biomarker to be detected may serve as the diagnostic composition. Accordingly, the diagnostic composition may further comprise means for detection of the metabolites as specified elsewhere in this description. Alternatively, if detection means such as MS or NMR based techniques are used, the molecular species which serves as an indicator for the risk condition will be the at least one biomarker comprised by the test sample to be investigated. Thus, the at least one biomarker referred to in accordance with the present invention shall serve itself as a diagnostic composition due to its identification as a biomarker.

Further, it will be understood that the present invention, in principle, relates to the use of at least one biomarker from Tables 1A, 1a, 1B, 1b, 2A, 2a, 2b, 3A, 3a, 3B, 3b, 4A, 4a, 4B or 4b in a sample of a subject suspected to suffer from liver disease for diagnosing liver disease or the predisposition therefor as set forth above in detail.

Particularly, the present invention relates to the use of at least one biomarker from Tables 1A, 1a, 1B, 1b, 3A, 3a, 3B, 3b, 4A, 4a, 4B or 4b in a sample of a subject suspected to suffer from fatty liver disease for diagnosing fatty liver disease or the predisposition therefor as set forth above in detail.

Particularly, the present invention relates to the use of at least one biomarker from Tables 2A, 2a or 2b in a sample of a subject suspected to suffer from inflammatory liver disease for diagnosing inflammatory liver disease or the predisposition therefor as set forth above in detail.

Further, it will be understood that the present invention, in principle, relates to the use of at least one biomarker from Tables 5A or 5B in a sample of a subject suspected to suffer from either NAFLD or NASH for differentiating between NAFLD and NASH in said subject.

All references cited herein are herewith incorporated by reference with respect to their disclosure content in general or with respect to the specific disclosure contents indicated above.

EXAMPLES

The invention will now be illustrated by the following Examples which are not intended to restrict or limit the scope of this invention.

Example 1: Sample Preparation and MS Analysis

Liver samples obtained by biopsy from 19 patients with diagnosed fatty liver disease or accompanying inflammation and 16 non-steatotic control patients were analyzed. Of the 19 patients, 7 showed NAFLD, 7 patients showed NASH and 5 carried a liver inflammation. Plasma samples from 27 patients with diagnosed fatty liver disease or accompanying inflammation and 18 non-steatotic control patients were analyzed. Of the 27 patients, 8 showed NAFLD, 12 patients showed NASH and 7 carried a liver inflammation.

The samples were prepared in the following way:

Proteins were separated by precipitation from blood plasma or from extracts obtained by solvent extraction of the freeze-dried liver tissue material. After addition of water and a mixture of ethanol and dichlormethan the remaining sample was fractioned into an aqueous, polar phase (polar fraction) and an organic, lipophilic phase (lipid fraction).

Usually, a biomarker is present in a single phase/fraction only, which is obvious to the person skilled in the art due to the nature of the respective metabolites. Some biomarkers, however, may be present in both phases/fractions. If the amount of these biomarkers was decreased or increased in only one of the analyzed fractions (e.g. the amount of Glycerol-3-phosphate, see Table 1A), the fraction in which decreased or increased amounts were observed was indicated in the following tables. In the context of the present invention, it is particularly preferred to determine the amount of these biomarkers in the fraction of a sample as indicated in the tables below.

For the transmethanolysis of the lipid extracts a mixture of 140 µl of chloroform, 37 µl of hydrochloric acid (37% by weight HCl in water), 320 µl of methanol and 20 µl of toluene was added to the evaporated extract. The vessel was sealed tightly and heated for 2 hours at 100° C., with shaking. The solution was subsequently evaporated to dryness. The residue was dried completely.

The methoximation of the carbonyl groups was carried out by reaction with methoxyamine hydrochloride (20 mg/ml in pyridine, 100 µl for 1.5 hours at 60° C.) in a tightly sealed vessel. 20 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 100 µl of N-methyl-N-(trimethylsilyl)-2,2,2-trifluoroacetamide (MSTFA) was carried out for 30 minutes at 60° C., again in the tightly sealed vessel. The final volume before injection into the GC was 220 µl.

For the polar phase the derivatization was performed in the following way: The methoximation of the carbonyl groups was carried out by reaction with methoxyamine hydrochloride (20 mg/ml in pyridine, 50 µl for 1.5 hours at 60° C.) in a tightly sealed vessel. 10 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 50 µl of N-methyl-N-(trimethylsilyl)-2,2,2-trifluoroacetamide (MSTFA) was carried out for 30 minutes at 60° C., again in the tightly sealed vessel. The final volume before injection into the GC was 110 µl.

The GC-MS systems consist of an Agilent 6890 GC coupled to an Agilent 5973 MSD. The autosamplers are CompiPal or GCPal from CTC.

For the analysis usual commercial capillary separation columns (30 m×0.25 mm×0.25 µm) with different polymethyl-siloxane stationary phases containing 0% up to 35% of aromatic moieties, depending on the analysed sample materials and fractions from the phase separation step, were used (for example: DB-1 ms, HP-5 ms, DB-XLB, DB-35 ms, Agilent Technologies). Up to 1 µL of the final volume was injected splitless and the oven temperature program was started at 70° C. and ended at 340° C. with different heating rates depending on the sample material and fraction from the phase separation step in order to achieve a sufficient chromatographic separation and number of scans within each analyte peak. Furthermore RTL (Retention Time Locking, Agilent Technologies) was used for the analysis and usual GC-MS standard conditions, for example constant flow with nominal 1 to 1.7 ml/min. and helium as the mobile phase gas, ionisation was done by electron impact with 70 eV, scanning within a m/z range from 15 to 600 with scan rates from 2.5 to 3 scans/sec and standard tune conditions.

The HPLC-MS systems consisted of an Agilent 1100 LC system (Agilent Technologies, Waldbronn, Germany) coupled with an API 4000 Mass spectrometer (Applied Biosystem/MDS SCIEX, Toronto, Canada). HPLC analysis was performed on commercially available reversed phase separation columns with C18 stationary phases (for example: GROM ODS 7 pH, Thermo Betasil C18). Up to 10 µL of the final sample volume of evaporated and reconstituted polar and lipophilic phase was injected and separation was performed with gradient elution using methanol/water/formic acid or acetonitrile/water/formic acid gradients at a flowrate of 200 µL/min.

Mass spectrometry was carried out by electrospray ionisation in positive mode for the nonpolar (lipid) fraction and negative mode for the polar fraction using multiple-reaction-monitoring-(MRM)-mode and fullscan from 100-1000 amu.

Analysis of steroids and catecholamines in plasma samples:

Steroids and their metabolites were measured by online SPE-LC-MS (Solid phase extraction-LC-MS). Catecholamines and their metabolites were measured by online SPE-LC-MS as described by Yamada et al [21]. Yamada H, Yamahara A, Yasuda S, Abe M, Oguri K, Fukushima S, Ikeda-Wada S: Dansyl chloride derivatization of methamphetamine: a methode with advantages for screening and analysis of methamphetamine in urine. Journal of Analytical Toxicology, 26(1): 17-22 (2002)

Example 2: Data Evaluation

Serum samples were analyzed in randomized analytical sequence design with pooled samples (so called "Pool") generated from aliquots of each sample. The raw peak data were normalized to the median of pool per analytical sequence to account for process variability (so called "ratios").

Following comprehensive analytical validation steps, the data for each analyte were normalized against data from pool samples. These samples were run in parallel through the whole process to account for process variability.

Groups were compared by Welch test (two-sided t-test assuming unequal variance). Ratios of median metabolite levels per group were derived indicating effect size and p-values of t-statistics indicating statistical significance. Regulation type was determined for each metabolite as "up" for increased (ratios >1, also called "fold" reference) within the respective group vs. reference and "down" for decreased (ratios <1, also called "fold" reference) vs. reference.

The results of the analyses are summarized in the following tables, below.

Additional chemical/physical properties of biomarkers marked with (*2) in the following Tables can be found in Table 6.

TABLE 1A

Metabolites increased in plasma in steatosis patients compared to controls

| METABOLITE_NAME | RATIO_OF_MEDIANS | PVALUE |
|---|---|---|
| Indole-3-propionic acid | 1.762 | 8.72E−02 |
| beta-Carotene | 1.950 | 3.90E−03 |
| TAG (C18:2, C18:3) (*2) | 1.920 | 1.60E−02 |
| Canthaxanthin | 1.836 | 2.18E−03 |
| Cryptoxanthin | 1.742 | 6.14E−03 |
| Glycerol, lipid fraction | 1.725 | 1.33E−02 |
| Creatine | 1.714 | 9.86E−04 |
| Docosahexaenoic acid (C22:cis[4, 7, 10, 13, 16, 19]6) | 1.711 | 5.82E−03 |
| Myristic acid (C14:0) | 1.699 | 3.96E−02 |
| erythro-C16-Sphingosine | 1.690 | 6.03E−02 |
| Aspartate | 1.647 | 5.48E−04 |
| TAG (C18:2, C18:2) (*2) | 1.582 | 5.24E−02 |
| Tricosanoic acid (C23:0) | 1.573 | 5.22E−02 |
| dihomo-gamma-Linolenic acid (C20:cis[8, 11, 14]3) | 1.552 | 2.91E−02 |
| Lignoceric acid (C24:0) | 1.536 | 3.34E−02 |
| Glycerol-3-phosphate, polar fraction | 1.500 | 1.05E−02 |
| Behenic acid (C22:0) | 1.459 | 2.41E−02 |
| Ceramide (d18:1, C24:0) | 1.449 | 5.32E−03 |
| gamma-Linolenic acid (C18:cis[6, 9, 12]3) | 1.391 | 2.90E−02 |
| Lysophosphatidylcholine (C18:2) | 1.389 | 4.35E−02 |
| Mannosamine | 1.384 | 4.20E−02 |
| Pentadecanol | 1.377 | 5.16E−02 |
| Linoleic acid (C18:cis[9, 12]2) | 1.373 | 3.58E−02 |
| myo-Inositol | 1.372 | 4.74E−02 |
| Eicosapentaenoic acid (C20:cis[5, 8, 11, 14, 17]5) | 1.362 | 6.68E−02 |
| Ketoleucine | 1.359 | 1.13E−02 |
| DAG (C18:1, C18:2) | 1.355 | 7.52E−02 |
| Tryptophan | 1.352 | 1.10E−02 |
| myo-Inositol-2-phosphate, lipid fraction (myo-Inositolphospholipids) | 1.345 | 7.48E−02 |
| Indole-3-lactic acid | 1.330 | 6.59E−03 |
| Glutamine | 1.323 | 3.33E−02 |

TABLE 1A-continued

Metabolites increased in plasma in steatosis patients compared to controls

| METABOLITE_NAME | RATIO_OF_MEDIANS | PVALUE |
|---|---|---|
| Glucosamine | 1.315 | 5.30E−02 |
| Alanine | 1.313 | 8.13E−04 |
| Eicosanoic acid (C20:0) | 1.307 | 3.67E−02 |
| Lysophosphatidylcholine (C18:0) | 1.298 | 2.15E−02 |
| Glycerol phosphate, lipid fraction | 1.289 | 8.38E−02 |
| Stearic acid (C18:0) | 1.267 | 1.21E−02 |
| Coenzyme Q10 | 1.264 | 5.45E−03 |
| Lysophosphatidylcholine (C17:0) | 1.259 | 9.04E−02 |
| Heptadecanoic acid (C17:0) | 1.251 | 3.59E−02 |
| gamma-Tocopherol | 1.245 | 7.02E−03 |
| myo-Inositol, lipid fraction | 1.245 | 2.96E−02 |
| Histidine | 1.235 | 7.50E−02 |
| Phosphatidylcholine (C18:0, C22:6) | 1.222 | 1.39E−03 |
| Cholestenol No 02 (*2) | 1.222 | 6.11E−02 |
| Cholesterol, total | 1.208 | 6.37E−02 |
| Sphingomyelin (d18:1, C24:0) | 1.190 | 5.56E−02 |
| Lysine | 1.183 | 5.97E−03 |
| Palmitic acid (C16:0) | 1.183 | 1.97E−02 |
| Oleic acid (C18:cis[9]1) | 1.182 | 8.90E−02 |
| Uric acid | 1.176 | 1.27E−02 |
| Ceramide (d18:1, C24:1) | 1.156 | 4.13E−02 |
| Elaidic acid (C18:trans[9]1) | 1.149 | 8.98E−02 |
| Lysophosphatidylcholine (C20:4) | 1.148 | 6.31E−02 |
| Cysteine | 1.137 | 5.25E−02 |
| Proline | 1.132 | 7.99E−02 |
| alpha-Tocopherol | 1.106 | 3.83E−02 |
| Phosphatidylcholine (C18:0, C18:1) | 1.101 | 5.16E−02 |
| conjugated Linoleic acid (C18:trans[9, 11]2) | 1.100 | 6.20E−02 |
| Methionine | 1.093 | 3.61E−02 |
| Lysophosphatidylcholine (C18:1) | 1.075 | 8.55E−02 |
| Phosphatidylcholine (C18:2, C20:4) | 1.067 | 1.79E−02 |
| Pyruvate | 1.062 | 1.24E−02 |
| Phosphatidylcholine (C16:0, C22:6) | 1.067 | 1.79E−02 |

TABLE 1a

Metabolites increased in liver tissue in steatosis patients compared to controls

| METABOLITE_NAME | Ratio of Medians | p-value |
|---|---|---|
| TAG (C18:1, C18:2) (*2) | 15.004 | 9.56E−06 |
| TAG (C16:0, C16:1) (*2) | 12.966 | 1.95E−05 |
| TAG (C16:0, C18:2) (*2) | 4.885 | 9.15E−05 |
| TAG (C18:2, C18:2) (*2) | 4.198 | 8.79E−06 |
| DAG (C18:1, C18:2) | 2.878 | 1.55E−04 |
| Myristic acid (C14:0) | 2.790 | 1.37E−02 |
| Lauric acid (C12:0) | 2.596 | 2.25E−02 |
| Coenzyme Q7 | 2.489 | 8.94E−04 |
| Glycerol, lipid fraction | 2.316 | 1.46E−03 |
| gamma-Tocopherol | 2.230 | 6.07E−03 |
| Palmitoleic acid (C16:cis[9]1) | 2.063 | 1.22E−02 |
| 14-Methylhexadecanoic acid | 2.037 | 1.50E−02 |
| Glucose-6-phosphate | 1.916 | 5.76E−02 |
| Oleic acid (C18:cis[9]1) | 1.916 | 3.24E−03 |
| Heptadecenoic acid (C17:cis[10]1) | 1.898 | 5.10E−03 |
| conjugated Linoleic acid (C18:trans[9, 11]2) | 1.775 | 5.85E−03 |
| Palmitic acid (C16:0) | 1.774 | 3.55E−03 |
| Eicosenoic acid (C20:cis[11]1) | 1.743 | 7.27E−03 |
| Fructose-1,6-diphosphate | 1.724 | 3.14E−02 |
| 17-Methyloctadecanoic acid | 1.692 | 9.39E−03 |

TABLE 1a-continued

Metabolites increased in liver tissue in steatosis patients compared to controls

| METABOLITE_NAME | Ratio of Medians | p-value |
|---|---|---|
| Linoleic acid (C18:cis[9, 12]2) | 1.599 | 6.49E−03 |
| Elaidic acid (C18:trans[9]1) | 1.598 | 9.09E−03 |
| Xanthosine | 1.570 | 4.36E−02 |
| Fructose-6-phosphate | 1.518 | 8.00E−03 |
| Coenzyme Q6 | 1.455 | 1.50E−03 |
| Heptadecanoic acid (C17:0) | 1.441 | 1.34E−02 |
| Ribulose-5-phosphate | 1.428 | 6.88E−03 |
| Uridine | 1.274 | 2.69E−02 |
| Glycerol-3-phosphate, polar fraction | 1.249 | 3.06E−02 |
| Eicosanoic acid (C20:0) | 1.214 | 2.82E−02 |
| Stearic acid (C18:0) | 1.209 | 9.35E−02 |

TABLE 1B

Metabolites decreased in plasma in steatosis patients compared to controls

| METABOLITE_NAME | RATIO_OF_MEDIANS | PVALUE |
|---|---|---|
| Sorbitol | 0.147 | 4.38E−02 |
| 3-Hydroxybutyrate | 0.399 | 1.00E−02 |
| Maltose | 0.655 | 5.94E−02 |
| Mannose | 0.840 | 9.58E−02 |
| Phosphatidylcholine (C16:0, C18:2) | 0.973 | 4.09E−02 |

TABLE 1b

Metabolites decreased in liver tissue in steatosis patients compared to controls

| METABOLITE_NAME | Ratio of medians | p-value |
|---|---|---|
| Pyridoxine | 0.526 | 7.58E−02 |
| myo-Inositol-2-phosphate | 0.579 | 1.24E−02 |
| 3-Hydroxybutyrate | 0.581 | 2.67E−02 |
| Ribose | 0.643 | 5.62E−02 |
| Cholic acid | 0.671 | 8.64E−02 |
| Nicotineamide adenine dinucleotide, reduced (NADH) | 0.678 | 8.43E−02 |
| 7-Methylguanine | 0.703 | 3.20E−02 |
| Ribonic acid | 0.713 | 6.18E−02 |
| Hexadecanol | 0.716 | 1.67E−02 |
| Pantothenic acid | 0.795 | 5.34E−02 |
| Isopentenyl pyrophosphate (IPP) | 0.813 | 8.89E−02 |
| myo-Inositol | 0.827 | 6.30E−02 |
| Nicotinic acid | 0.846 | 7.55E−02 |

TABLE 2A

Metabolites increased in plasma in inflammatory liver disease patients (inflammatory liver disease not accompanied by steatosis) compared to controls

| METABOLITE_NAME | RATIO_OF_MEDIANS | PVALUE |
|---|---|---|
| beta-Carotene | 2.286 | 1.85E−02 |
| Lignoceric acid (C24:0) | 1.890 | 4.33E−02 |
| Canthaxanthin | 1.843 | 4.59E−02 |
| erythro-C16-Sphingosine | 1.786 | 7.46E−02 |
| Aspartate | 1.743 | 5.34E−02 |
| Serotonin (5-HT) | 1.719 | 2.68E−02 |
| Tricosanoic acid (C23:0) | 1.694 | 2.02E−02 |
| Cryptoxanthin | 1.632 | 7.97E−02 |
| Glycerol-3-phosphate, polar fraction | 1.630 | 1.43E−02 |

TABLE 2A-continued

Metabolites increased in plasma in inflammatory liver disease patients (inflammatory liver disease not accompanied by steatosis) compared to controls

| METABOLITE_NAME | RATIO_OF_MEDIANS | PVALUE |
|---|---|---|
| Behenic acid (C22:0) | 1.613 | 3.84E−02 |
| Mannosamine | 1.570 | 5.15E−03 |
| 3,4-Dihydroxyphenylacetic acid (DOPAC) | 1.553 | 5.57E−02 |
| TAG (C18:2, C18:3) (*2) | 1.549 | 7.12E−02 |
| Glucose-6-phosphate | 1.530 | 5.16E−02 |
| Homovanillic acid (HVA) | 1.496 | 6.35E−02 |
| Glucosamine | 1.495 | 1.69E−03 |
| Normetanephrine | 1.461 | 2.86E−02 |
| Creatine | 1.461 | 1.18E−02 |
| Linoleic acid (C18:cis[9,12]2) | 1.406 | 7.25E−02 |
| Eicosanoic acid (C20:0) | 1.400 | 7.48E−02 |
| Tryptophan | 1.384 | 1.43E−02 |
| myo-Inositol-2-phosphate | 1.347 | 8.38E−02 |
| Serine | 1.336 | 2.90E−02 |
| Glutamine | 1.318 | 7.89E−02 |
| Arachidonic acid (C20:cis[5,8,11,14]4) | 1.313 | 4.65E−02 |
| Indole-3-lactic acid | 1.294 | 4.63E−02 |
| Alanine | 1.277 | 2.05E−02 |
| Histidine | 1.277 | 3.36E−02 |
| Stearic acid (C18:0) | 1.271 | 6.54E−02 |
| Lysophosphatidylcholine (C18:0) | 1.254 | 4.48E−02 |
| Lysine | 1.205 | 6.31E−03 |
| Phosphate (inorganic and from organic phosphates) | 1.200 | 9.54E−02 |
| Sphingomyelin (d18:1,C24:0) | 1.200 | 8.29E−02 |
| Pyruvate | 1.186 | 7.79E−02 |
| 3,4-Dihydroxyphenylglycol (DOPEG) | 1.155 | 8.33E−02 |
| Phosphatidylcholine (C18:0, C22:6) | 1.130 | 6.04E−02 |
| conjugated Linoleic acid (C18:trans[9,11]2) | 1.112 | 7.96E−02 |
| Citrate | 1.106 | 5.74E−02 |
| Methionine | 1.099 | 3.78E−02 |
| Taurine | 1.077 | 6.17E−02 |
| Phosphatidylcholine (C18:0, C20:4) | 1.026 | 1.15E−02 |
| Lysophosphatidylcholine (C16:0) | 1.016 | 9.11E−02 |

TABLE 2a

Metabolites increased in liver tissue in inflammatory liver disease patients (inflammatory liver disease not accompanied by steatosis) compared to controls

| METABOLITE_NAME | Ratio of medians | p-value |
|---|---|---|
| TAG (C18:1, C18:2) (*2) | 12.986 | 1.34E−03 |
| TAG (C16:0, C16:1) (*2) | 10.448 | 2.31E−03 |
| TAG (C18:2, C18:2) (*2) | 4.765 | 6.10E−04 |
| TAG (C16:0, C18:2) (*2) | 4.001 | 1.39E−02 |
| Myristic acid (C14:0) | 3.738 | 1.78E−02 |
| Sedoheptulose-7-phosphate | 3.405 | 1.76E−02 |
| Glucose-6-phosphate | 3.067 | 3.10E−02 |
| DAG (C18:1, C18:2) | 2.927 | 5.78E−03 |
| Palmitoleic acid (C16:cis[9]1) | 2.886 | 1.11E−02 |
| 14-Methylhexadecanoic acid | 2.631 | 2.03E−02 |
| Heptadecenoic acid (C17:cis[10]1) | 2.614 | 1.42E−03 |
| Coenzyme Q7 | 2.588 | 1.49E−02 |
| Lauric acid (C12:0) | 2.578 | 7.04E−02 |
| Glycerol, lipid fraction | 2.559 | 1.16E−02 |
| Fructose-1,6-diphosphate | 2.342 | 2.08E−02 |
| Oleic acid (C18:cis[9]1) | 2.271 | 4.33E−03 |
| Phosphocreatine | 2.238 | 7.91E−02 |
| Fructose-6-phosphate | 2.134 | 3.62E−02 |
| conjugated Linoleic acid (C18:trans[9,11]2) | 1.927 | 2.77E−02 |

TABLE 2a-continued

Metabolites increased in liver tissue in inflammatory liver disease patients (inflammatory liver disease not accompanied by steatosis) compared to controls

| METABOLITE_NAME | Ratio of medians | p-value |
|---|---|---|
| Xanthosine | 1.893 | 5.35E−02 |
| Ribulose-5-phosphate | 1.836 | 1.39E−03 |
| Serine, lipid fraction | 1.672 | 7.32E−02 |
| Palmitic acid (C16:0) | 1.659 | 4.75E−02 |
| Linoleic acid (C18:cis[9,12]2) | 1.654 | 4.49E−02 |
| Elaidic acid (C18:trans[9]1) | 1.595 | 7.02E−02 |
| Inosine | 1.569 | 1.12E−03 |
| Coenzyme Q6 | 1.568 | 4.50E−03 |
| Uridine | 1.516 | 1.02E−02 |
| Heptadecanoic acid (C17:0) | 1.419 | 8.81E−02 |
| Glycerol-3-phosphate, polar fraction | 1.289 | 9.41E−02 |

TABLE 2b

Metabolites decreased in liver tissue in inflammatory liver disease patients (inflammatory liver disease not accompanied by steatosis) compared to controls

| METABOLITE_NAME | Ratio of medians | p-value |
|---|---|---|
| 3-Hydroxybutyrate | 0.365 | 7.21E−04 |
| myo-Inositol-2-phosphate | 0.502 | 3.22E−02 |
| 2-Hydroxybutyrate | 0.627 | 5.02E−02 |
| Hexadecanol | 0.636 | 3.22E−02 |
| Isopentenyl pyrophosphate (IPP) | 0.684 | 3.55E−02 |
| Nervonic acid (C24:cis[15]1) | 0.787 | 9.47E−02 |
| Phosphatidylcholine (C16:0, C18:2) | 0.955 | 6.41E−02 |

TABLE 3A

Metabolites increased in plasma in NASH patients compared to controls

| METABOLITE_NAME | RATIO_OF_MEDIANS | PVALUE |
|---|---|---|
| TAG (C18:2, C18:3) (*2) | 2.781 | 9.40E−03 |
| Glycerol, lipid fraction | 2.312 | 2.51E−02 |
| Canthaxanthin | 2.006 | 4.63E−03 |
| beta-Carotene | 1.973 | 5.08E−03 |
| TAG (C18:2, C18:2) (*2) | 1.897 | 3.17E−02 |
| Cryptoxanthin | 1.852 | 8.08E−03 |
| Creatine | 1.779 | 8.95E−03 |
| Docosahexaenoic acid (C22:cis[4,7,10,13,16,19]6) | 1.776 | 9.89E−03 |
| Myristic acid (C14:0) | 1.763 | 3.81E−02 |
| Ceramide (d18:1,C24:0) | 1.618 | 1.96E−02 |
| Lysophosphatidylcholine (C18:2) | 1.514 | 4.49E−02 |
| Pentadecanol | 1.513 | 4.43E−02 |
| TAG (C16:0, C16:1) (*2) | 1.512 | 9.69E−02 |
| myo-Inositol-2-phosphate, lipid fraction (myo-Inositolphospholipids) | 1.493 | 3.77E−02 |
| Aspartate | 1.486 | 1.13E−02 |
| gamma-Tocopherol | 1.436 | 5.09E−03 |
| DAG (C18:1, C18:2) | 1.436 | 8.29E−02 |
| Alanine | 1.389 | 7.97E−03 |
| myo-Inositol | 1.378 | 1.63E−02 |
| Indole-3-lactic acid | 1.378 | 3.72E−02 |
| Palmitic acid (C16:0) | 1.372 | 5.90E−02 |
| Behenic acid (C22:0) | 1.371 | 9.28E−02 |
| dihomo-gamma-Linolenic acid (C20:cis[8,11,14]3) | 1.351 | 6.46E−02 |
| Ketoleucine | 1.351 | 3.00E−02 |
| gamma-Linolenic acid (C18:cis[6,9,12]3) | 1.345 | 4.12E−02 |
| Linoleic acid (C18:cis[9,12]2) | 1.340 | 5.69E−02 |
| myo-Inositol, lipid fraction | 1.340 | 2.10E−02 |

TABLE 3A-continued

Metabolites increased in plasma in NASH patients compared to controls

| METABOLITE_NAME | RATIO_OF_MEDIANS | PVALUE |
|---|---|---|
| Heptadecanoic acid (C17:0) | 1.322 | 5.87E−02 |
| Lysophosphatidylcholine (C18:0) | 1.312 | 2.10E−02 |
| Coenzyme Q10 | 1.294 | 6.10E−03 |
| Lysophosphatidylcholine (C18:1) | 1.293 | 8.57E−02 |
| Ceramide (d18:1,C24:1) | 1.273 | 7.53E−02 |
| Stearic acid (C18:0) | 1.263 | 3.02E−02 |
| Phosphatidylcholine (C18:0, C22:6) | 1.235 | 2.99E−03 |
| Tryptophan | 1.227 | 6.07E−02 |
| Uric acid | 1.158 | 5.35E−03 |
| Phosphatidylcholine (C18:0, C18:1) | 1.146 | 5.75E−02 |
| Proline | 1.134 | 6.28E−02 |
| Cysteine | 1.130 | 9.73E−02 |
| Pyruvate | 1.110 | 1.44E−02 |
| Lysine | 1.071 | 7.79E−02 |
| Phosphatidylcholine (C18:2, C20:4) | 1.063 | 3.08E−02 |
| Phosphatidylcholine (C16:0, C22:6) | 1.063 | 3.08E−02 |

TABLE 3a

Metabolites increased in liver tissue in NASH patients compared to controls

| METABOLITE_NAME | Ratio of medians | p-value |
|---|---|---|
| TAG (C18:1, C18:2) (*2) | 29.319 | 2.13E−05 |
| TAG (C16:0, C16:1) (*2) | 28.683 | 1.60E−05 |
| TAG (C18:2, C18:2) (*2) | 5.982 | 4.60E−05 |
| TAG (C16:0, C18:2) (*2) | 5.934 | 1.07E−03 |
| Lauric acid (C12:0) | 5.809 | 7.55E−04 |
| Myristic acid (C14:0) | 4.999 | 1.44E−03 |
| DAG (C18:1, C18:2) | 3.811 | 3.62E−04 |
| Glycerol, lipid fraction | 3.534 | 2.76E−04 |
| Coenzyme Q7 | 3.176 | 1.87E−03 |
| Palmitoleic acid (C16:cis[9]1) | 2.954 | 3.32E−03 |
| Oleic acid (C18:cis[9]1) | 2.873 | 1.92E−04 |
| Heptadecenoic acid (C17:cis[10]1) | 2.861 | 2.42E−04 |
| Palmitic acid (C16:0) | 2.503 | 1.95E−04 |
| Eicosenoic acid (C20:cis[11]1) | 2.426 | 1.73E−03 |
| 14-Methylhexadecanoic acid | 2.196 | 4.15E−02 |
| 17-Methyloctadecanoic acid | 2.193 | 3.12E−03 |
| conjugated Linoleic acid (C18:trans[9,11]2) | 2.010 | 1.24E−02 |
| Linoleic acid (C18:cis[9,12]2) | 1.976 | 2.68E−03 |
| Elaidic acid (C18:trans[9]1) | 1.968 | 6.30E−03 |
| Heptadecanoic acid (C17:0) | 1.781 | 2.40E−03 |
| Coenzyme Q6 | 1.654 | 8.29E−04 |
| Eicosadienoic acid (C20:2) No 02 (*2) | 1.553 | 4.04E−02 |
| Eicosanoic acid (C20:0) | 1.463 | 9.53E−04 |
| Stearic acid (C18:0) | 1.449 | 1.35E−02 |
| Glycerol-3-phosphate, polar fraction | 1.281 | 7.72E−02 |

TABLE 3B

Metabolites decreased in plasma in NASH patients compared to controls

| METABOLITE_NAME | RATIO_OF_MEDIANS | PVALUE |
|---|---|---|
| Sorbitol | 0.182 | 6.83E−03 |
| 3-Hydroxybutyrate | 0.218 | 5.09E−03 |
| Mannose | 0.700 | 3.73E−02 |
| Phosphatidylcholine (C16:0, C18:2) | 0.964 | 3.68E−02 |

TABLE 3b

Metabolites decreased in liver tissue in NASH patients compared to controls

| METABOLITE_NAME | Ratio of medians | p-value |
|---|---|---|
| 3-Hydroxybutyrate | 0.409 | 8.68E-04 |
| 7-Methylguanine | 0.558 | 7.06E-03 |
| Glycerol phosphate, lipid fraction | 0.559 | 3.52E-02 |
| Nicotineamide adenine dinucleotide, reduced (NADH) | 0.566 | 6.21E-02 |
| Ribose, lipid fraction | 0.591 | 6.54E-02 |
| Hexadecanol | 0.678 | 5.76E-02 |
| Hypoxanthine | 0.712 | 7.98E-02 |
| Coenzyme Q9 | 0.726 | 5.96E-02 |
| Pantothenic acid | 0.734 | 5.73E-02 |
| Nicotinic acid | 0.748 | 2.25E-02 |
| myo-Inositol | 0.752 | 3.41E-02 |
| Nicotinamide | 0.793 | 8.04E-02 |
| Flavine adenine dinucleotide (FAD) | 0.797 | 9.90E-02 |
| Phosphate, lipid fraction | 0.818 | 9.42E-02 |

TABLE 4A

Metabolites increased in plasma in NAFLD patients compared to controls

| METABOLITE_NAME | RATIO_OF_MEDIANS | PVALUE |
|---|---|---|
| Creatine | 2.227 | 7.07E-03 |
| Phosphocreatine | 2.156 | 2.22E-02 |
| Glycerol-3-phosphate, polar fraction | 1.942 | 1.61E-02 |
| Docosahexaenoic acid (C22:cis[4,7,10,13,16,19]6) | 1.872 | 2.24E-03 |
| Eicosapentaenoic acid (C20:cis[5,8,11,14,17]5) | 1.821 | 9.85E-03 |
| Cryptoxanthin | 1.788 | 2.05E-02 |
| Aspartate | 1.755 | 1.96E-02 |
| erythro-C16-Sphingosine | 1.642 | 2.50E-02 |
| Glucose-6-phosphate | 1.604 | 3.67E-02 |
| Canthaxanthin | 1.577 | 3.92E-02 |
| Behenic acid (C22:0) | 1.566 | 4.65E-02 |
| Tricosanoic acid (C23:0) | 1.563 | 5.64E-02 |
| dihomo-gamma-Linolenic acid (C20:cis[8,11,14]3) | 1.489 | 6.14E-02 |
| Lignoceric acid (C24:0) | 1.431 | 4.15E-02 |
| Coenzyme Q10 | 1.405 | 1.34E-02 |
| Ceramide (d18:1, C24:0) | 1.397 | 3.52E-02 |
| Serine | 1.370 | 3.72E-02 |
| Ketoleucine | 1.362 | 9.08E-03 |
| Phosphatidylcholine (C18:0, C22:6) | 1.360 | 8.09E-04 |
| Indole-3-lactic acid | 1.358 | 6.13E-02 |
| Eicosanoic acid (C20:0) | 1.351 | 6.63E-02 |
| Cholestenol No 02 (*2) | 1.347 | 7.71E-02 |
| Lysophosphatidylcholine (C18:0) | 1.321 | 8.13E-02 |
| Histidine | 1.321 | 7.25E-02 |
| Ceramide (d18:1, C24:1) | 1.315 | 5.11E-02 |
| Glutamine | 1.310 | 3.99E-02 |
| Arginine | 1.299 | 4.35E-03 |
| beta-Carotene | 1.262 | 7.88E-02 |
| gamma-Tocopherol | 1.245 | 3.73E-02 |
| Cholesterol, total | 1.216 | 7.59E-02 |
| Sphingomyelin (d18:1, C24:0) | 1.213 | 1.86E-02 |
| Lysine | 1.211 | 9.45E-03 |
| Alanine | 1.139 | 6.89E-02 |
| alpha-Tocopherol | 1.122 | 3.87E-02 |
| Phosphatidylcholine (C18:0, C18:1) | 1.114 | 5.66E-02 |
| Palmitic acid (C16:0) | 1.090 | 9.59E-02 |
| Phosphatidylcholine (C18:2, C20:4) | 1.068 | 3.28E-03 |
| Phosphatidylcholine No 02 (*2) | 1.054 | 6.59E-02 |
| Phosphatidylcholine (C18:0, C20:4) | 1.013 | 7.14E-02 |
| Phosphatidylcholine (C16:0, C22:6) | 1.068 | 3.28E-03 |

TABLE 4a

Metabolites increased in liver tissue in NAFLD patients compared to controls

| METABOLITE_NAME | Ratio of medians | p-value |
|---|---|---|
| TAG (C18:1, C18:2) (*2) | 8.804 | 2.97E-03 |
| TAG (C16:0, C16:1) (*2) | 7.202 | 5.12E-03 |
| TAG (C16:0, C18:2) (*2) | 3.728 | 1.41E-02 |
| gamma-Tocopherol | 2.897 | 8.11E-03 |
| TAG (C18:2, C18:2) (*2) | 2.851 | 9.20E-03 |
| DAG (C18:1, C18:2) | 2.184 | 2.29E-02 |
| Coenzyme Q7 | 1.916 | 5.95E-02 |
| Fructose-1,6-diphosphate | 1.768 | 9.49E-02 |
| O-Phosphoethanolamine | 1.555 | 2.88E-02 |
| Malate | 1.517 | 9.27E-02 |
| Ribulose-5-phosphate | 1.412 | 3.39E-02 |
| Taurine | 1.333 | 4.05E-02 |
| Creatine | 1.330 | 7.03E-02 |

TABLE 4B

Metabolites decreased in plasma in NAFLD patients compared to controls

| METABOLITE_NAME | RATIO_OF_MEDIANS | PVALUE |
|---|---|---|
| Glycochenodeoxycholic acid | 0.174 | 7.26E-02 |
| Glucose, lipid fraction | 0.583 | 7.12E-02 |
| Kynurenic acid | 0.585 | 8.65E-02 |
| Cortisol | 0.644 | 9.12E-02 |
| Sphingomyelin (d18:1, C16:0) | 0.978 | 9.73E-03 |

TABLE 4b

Metabolites decreased in liver tissue in NAFLD patients compared to controls

| METABOLITE_NAME | Ratio of medians | p-value |
|---|---|---|
| Pyridoxine | 0.376 | 5.53E-02 |
| Cholic acid | 0.473 | 1.78E-02 |
| myo-Inositol-2-phosphate | 0.588 | 7.64E-02 |

TABLE 5A

Metabolites increased in plasma NASH patients compared to NAFLD patients

| METABOLITE_NAME | RATIO_OF_MEDIANS | PVALUE |
|---|---|---|
| Glycochenodeoxycholic acid | 8.681 | 9.92E-02 |
| Kynurenic acid | 1.885 | 7.88E-03 |
| Glucose, lipid fraction | 1.738 | 1.25E-02 |
| Glycolate | 1.189 | 2.73E-02 |
| trans-4-Hydroxyproline | 1.169 | 3.47E-02 |

TABLE 5A-continued

Metabolites increased in plasma NASH patients compared to NAFLD patients

| METABOLITE_NAME | RATIO_OF_MEDIANS | PVALUE |
| --- | --- | --- |
| Pseudouridine | 1.163 | 3.75E-02 |
| Pyruvate | 1.112 | 8.28E-02 |
| Sphingomyelin (d18:1, C16:0) | 1.016 | 1.43E-02 |

TABLE 5B

Metabolites decreased in plasma NASH patients compared to NAFLD patients

| METABOLITE_NAME | RATIO_OF_MEDIANs | PVALUE |
| --- | --- | --- |
| 3-Hydroxybutyrate | 0.275 | 4.36E-02 |
| Phosphocreatine | 0.534 | 2.76E-02 |
| Eicosapentaenoic acid (C20:cis[5,8,11,14,17]5) | 0.642 | 7.15E-02 |
| Serine | 0.764 | 8.92E-02 |
| Arginine | 0.831 | 1.02E-02 |
| Phosphatidylcholine (C18:2, C20:4) | 0.990 | 6.80E-02 |
| Phosphatidylcholine (C16:0, C22:6) | 0.990 | 6.80E-02 |

TABLE 6

Additional chemical/physical properties of biomarkers marked with (*2) in the tables above.

| Metabolite Name | Description |
| --- | --- |
| Cholestenol No 02 | Cholestenol No 02 represents a Cholestenol isomer. It exhibits the following characteristic ionic fragments when detected with GC/MS, applying electron impact (EI) ionization mass spectrometry, after acidic methanolysis and derivatisation with 2% O-methylhydroxylamine-hydrochlorid in pyridine and subsequently with N-methyl-N-trimethylsilyltrifluoracetamid: MS (EI, 70 eV): m/z (%): 143 (100), 458 (91), 73 (68), 81 (62), 95 (36), 185 (23), 327 (23), 368 (20), 255 (15), 429 (15). |
| Eicosadienoic acid (C20:2) No 02 | Eicosadienoic acid (C20:2) No 02 represents an Eicosadienoic acid isomer. It exhibits the following characteristic ionic fragments when detected with GC/MS, applying electron impact (EI) ionization mass spectrometry, after acidic methanolysis and derivatisation with 2% O-methylhydroxylamine-hydrochlorid in pyridine and subsequently with N-methyl-N-trimethylsilyltrifluoracetamid: MS (EI, 70 eV): m/z (%): 81 (100), 57 (98), 43 (92), 67 (85), 41 (80), 55 (74), 82 (66), 95 (64), 110 (39), 109 (39). |
| Phosphatidylcholine No 02 | Phosphatidylcholine No 02 represents the sum parameter of phosphatidylcholines. It exhibits the following characteristic ionic species when detected with LC/MS, applying electro-spray ionization (ESI) mass spectrometry: mass-to-charge ratio (m/z) of the positively charged ionic species is 808.4 (+/−0.5). |
| TAG (C18:2, C18:2) | TAG (C18:2, C18:2) represents the sum parameter of tri-acylglycerides containing the combination of two C18:2 fatty acid units. It exhibits the following characteristic ionic species when detected with LC/MS, applying electro-spray ionization (ESI) mass spectrometry: mass-to-charge ratio (m/z) of the positively charged ionic species is 599.6 (+/−0.5). |
| TAG (C16:0, C16:1) | TAG (C16:0, C16:1) represents the sum parameter of tri-acylglycerides containing the combination of a C16:0 fatty acid unit and a C16:1 fatty acid unit. It exhibits the following characteristic ionic species when detected with LC/MS, applying electro-spray ionization (ESI) mass spectrometry: mass-to-charge ratio (m/z) of the positively charged ionic species is 549.6 (+/−0.5). |
| TAG (C18:2, C18:3) | TAG (C18:2, C18:3) represents the sum parameter of tri-acylglycerides containing the combination of a C18:2 fatty acid unit and a C18:3 fatty acid unit. It exhibits the following characteristic ionic species when detected with LC/MS, applying electro-spray ionization (ESI) mass spectrometry: mass-to-charge ratio (m/z) of the positively charged ionic species is 597.6 (+/−0.5). |

TABLE 6-continued

Additional chemical/physical properties of biomarkers marked with (*2) in the tables above.

| Metabolite Name | Description |
| --- | --- |
| TAG (C16:0, C18:2) | TAG (C16:0, C18:2) represents the sum parameter of tri-acylglycerides containing the combination of a C16:0 fatty acid unit and a C18:2 fatty acid unit. It exhibits the following characteristic ionic species when detected with LC/MS, applying electro-spray ionization (ESI) mass spectrometry: mass-to-charge ratio (m/z) of the positively charged ionic species is 575.4 (+/−0.5). |
| TAG (C18:2, C18:2) | TAG (C18:2, C18:2) represents the sum parameter of tri-acylglycerides containing the combination of two C18:2 fatty acid units. It exhibits the following characteristic ionic species when detected with LC/MS, applying electro-spray ionization (ESI) mass spectrometry: mass-to-charge ratio (m/z) of the positively charged ionic species is 599.6 (+/−0.5). |
| TAG (C16:0, C16:1) | TAG (C16:0, C16:1) represents the sum parameter of tri-acylglycerides containing the combination of a C16:0 fatty acid unit and a C16:1 fatty acid unit. It exhibits the following characteristic ionic species when detected with LC/MS, applying electro-spray ionization (ESI) mass spectrometry: mass-to-charge ratio (m/z) of the positively charged ionic species is 549.4 (+/−0.5). |
| TAG (C18:1, C18:2) | TAG (C18:1, C18:2) represents the sum parameter of tri-acylglycerides containing the combination of a C18:1 fatty acid unit and a C18:2 fatty acid unit. It exhibits the following characteristic ionic species when detected with LC/MS, applying electro-spray ionization (ESI) mass spectrometry: mass-to-charge ratio (m/z) of the positively charged ionic species is 601.4 (+/−0.5). |

The invention claimed is:

1. A method for differentiating between non-alcoholic steatohepatitis (NASH) and non-alcoholic fatty liver disease (NAFLD) in a subject comprising:
   (a) determining in a sample of a subject suspected to suffer from either NASH or NAFLD the amount of at least one biomarker from
      (1) Glycochenodeoxycholic acid, Glycolate, trans-4-Hydroxyproline, Pseudouridine, or Sphingomyelin (d18:1, C16:0) or
      (2) 3-Hydroxybutyrate, Phosphocreatine, Eicosapentaenoic acid (C20:cis[5,8,11,14,17]5), Serine, Arginine, Phosphatidylcholine (C18:2, C20:4), or Phosphatidylcholine (C16:0, C22:6); and
   (b) comparing the said amount of the at least one biomarker with a reference, whereby it is differentiated whether the subject suffers from NASH or NAFLD,
   wherein the reference is derived from a subject known to suffer from NAFLD or a subject known to suffer from NASH,
   wherein, when the reference is derived from a subject known to suffer from NAFLD, an increased amount of a biomarker from (a)(1) with respect to the reference is indicative for NASH or a decreased amount of a biomarker from (a)(2) with respect to the reference is indicative for NASH, and
   wherein, when the reference is derived from a subject known to suffer from NASH, a decreased amount of a biomarker from (a)(1) with respect to the reference is indicative for NAFLD or an increased amount of a biomarker from (a)(2) with respect to the reference is indicative for NAFLD.

* * * * *